US012714795B2

(12) United States Patent
Forman

(10) Patent No.: US 12,714,795 B2
(45) Date of Patent: Aug. 25, 2026

(54) GENE GUN

(71) Applicant: DAICEL CORPORATION, Osaka (JP)

(72) Inventor: David Michael Forman, Fountain Hills, AZ (US)

(73) Assignee: DAICEL CORPORATION, Osaka (JP)

( * ) Notice: Subject to any disclaimer, the term of this patent is extended or adjusted under 35 U.S.C. 154(b) by 1033 days.

(21) Appl. No.: 17/771,950

(22) PCT Filed: Oct. 29, 2020

(86) PCT No.: PCT/JP2020/040705

§ 371 (c)(1),
(2) Date: Apr. 26, 2022

(87) PCT Pub. No.: WO2021/085564

PCT Pub. Date: May 6, 2021

(65) Prior Publication Data

US 2022/0362473 A1 Nov. 17, 2022

Related U.S. Application Data

(60) Provisional application No. 62/928,280, filed on Oct. 30, 2019.

(51) Int. Cl.

| | |
|---|---|
| ***C06C 7/00*** | (2006.01) |
| ***A61M 5/20*** | (2006.01) |
| ***A61M 5/30*** | (2006.01) |

(52) U.S. Cl.
CPC ........ *A61M 5/3015* (2013.01); *A61M 5/2046* (2013.01); *C06C 7/00* (2013.01)

(58) Field of Classification Search
CPC .............................. A61M 5/30; A61M 5/2046
See application file for complete search history.

(56) References Cited

U.S. PATENT DOCUMENTS 4,727,808 A * 3/1988 Wang ........................ F42B 3/12 102/202.13
5,889,228 A 3/1999 Ewick et al.
(Continued)

FOREIGN PATENT DOCUMENTS

EP 0974037 A1 1/2000
EP 0974037 B1 * 11/2005 ................ F24B 3/13
(Continued)

OTHER PUBLICATIONS

International Search Report and Written Opinion issued in International Application No. PCT/JP2020/040705, dated Dec. 28, 2020.
(Continued)

*Primary Examiner* — William R Carpenter
(74) *Attorney, Agent, or Firm* — Knobbe, Martens, Olson & Bear, LLP

(57) ABSTRACT

An accelerator module is connected to an initiator module and generates supersonic waves from subsonic waves generated by the initiator module. The supersonic waves deliver particles to cells in tissues. The accelerator module may include a knocking-detonation transition metal and a detonation material. An example of the knocking-detonation transition metal is copper (I) 5-nitrotetrazolate. Another example of the knocking-detonation transition metal is lead azide. An example of the detonation material is pentaerythritol tetranitrate (PETN).

15 Claims, 15 Drawing Sheets

(56) References Cited

U.S. PATENT DOCUMENTS

| | | | | |
|---|---|---|---|---|
| 6,227,116 | B1 | 5/2001 | Dumenko | |
| 6,408,759 | B1 | 6/2002 | Ewick et al. | |
| 2004/0180442 | A1 | 9/2004 | Lin et al. | |
| 2006/0153804 | A1 | 7/2006 | Lively et al. | |
| 2010/0198146 | A1 | 8/2010 | Jagadeesh | |
| 2017/0197034 | A1 | 7/2017 | Lell et al. | |
| 2017/0216530 | A1 * | 8/2017 | Lell | A61M 5/30 |
| 2017/0314582 | A1 | 11/2017 | Lell | |

FOREIGN PATENT DOCUMENTS

| | | | | |
|---|---|---|---|---|
| JP | 2000-502036 | A | 2/2000 | |
| JP | 2001-523328 | A | 11/2001 | |
| JP | 2004-236657 | A | 8/2004 | |
| JP | 2006-503063 | A | 1/2006 | |
| JP | 2017-519570 | A | 7/2017 | |
| WO | WO 98/045663 | A1 | 10/1998 | |
| WO | WO-2004071558 | A1 * | 8/2004 | A61M 5/3015 |

OTHER PUBLICATIONS

Extended Search Report issued in EP Application No. 20882074.6, dated Oct. 5, 2023.

* cited by examiner

GENE GUN

The present application is a U.S. national phase application under 35 U.S.C. § 371 of International Application No. PCT/JP2020/040705, filed on Oct. 29, 2020, which claims the benefit of U.S. Provisional Patent Application No. 62/928,280 filed on Oct. 30, 2019 in the United States Patent and Trademark Office, the entire disclosure of each of which is incorporated herein by reference.

TECHNICAL FIELD

This disclosure relates to apparatuses and methods for gene therapy. More specifically, the apparatuses and methods relate to a biolistic particle delivery system for delivering exogenous DNA (transgenes) to cells.

BACKGROUND ART

A gene gun accelerates small doped metal particles to the highest possible velocity. The particles pass through tissue on their way to target cells. Because the particles have such a high velocity and density, and are so small, they penetrate through tissue without permanently damaging the tissue. What damage they do is readily repaired by the tissue due to the small size of the penetrating path. When they reach the target cells, the doping (consisting of DNA) is inserted into the nucleus of the cells.

Patent Document 1 discloses a gene gun that accelerates a solution containing a biological material using a gas to deliver the biological material into cells, without using metal particles.

CITATION LIST

Patent Document

Patent Document 1: JP 2004-236657 A

SUMMARY OF INVENTION

Technical Problem

The practical limit for accelerating particles today is the speed of sound in the gaseous medium that is used. The fastest existing technology accelerates particles in an atmosphere of helium to increase the speed of sound and thus the practical limit for particle speed. This limits the effectiveness of existing gene guns by limiting the depth of penetration of the particles (particle penetration depth is a function of particle velocity). The only other gas that has a higher speed of sound is hydrogen, but that would lead to flammability concerns.

Solution to Problem

In certain medical applications, it can be advantageous to utilize a biolistic particle delivery system. In certain embodiments, the gene gun relies on a phenomenon of detonation (explosion) to achieve doped metal particle velocities greater than the speed of sound in any gas. In certain embodiments, the gene gun creates a detonating wave that travels through a wall or wall segment but does not rupture the wall. The wave travels though the wall at the speed of sound in the wall material. For example, in certain embodiments, the wall is stainless steel. For stainless steel, the speed of sound is 5,790 m/s. On the other side of the wall are the doped metal particles. The doped metal particles are ejected at an initial velocity of the detonating (explosion) wave, namely 5,790 m/s in the example above. This is a substantial increase over the speed of sound in helium, which is 1,007 m/s.

An aspect is an accelerator module configured to be coupled to an initiator module and create a supersonic wave from a subsonic wave created by the initiator module. The supersonic wave is configured to deliver particles to cells within tissue. The accelerator module includes a body having a propagation axis and defining (demarcating, specifying) a receptacle with a bottom surface. The receptacle includes a first portion and a second portion disposed between the first portion and the bottom surface. The accelerator module further includes a first material disposed in the first portion, a second material disposed in the second portion, a wall segment at least partially defined between the bottom surface of the receptacle and an outer surface of the body, and a plurality of doped metal particles in contact with the outer surface of the body and generally aligned with the bottom surface along the propagation axis. The first material and the second material are configured to be ignited (triggered) by the subsonic wave created by the initiator module to create the supersonic wave. The supersonic wave is configured to pass through the wall segment to then accelerate the plurality of doped metal particles to a speed.

Certain aspects include where the speed is a supersonic speed.

Certain aspects include where the speed is sufficient to penetrate the cells within the tissue.

Certain aspects include where the first material is a deflagration-to-detonation transition material (DDT).

Certain aspects include where the deflagration-to-detonation transition material includes a dry powder (dry explosive).

Certain aspects include where the deflagration-to-detonation transition material includes lead azide.

Certain aspects include where the deflagration-to-detonation transition material includes copper (I) 5-nitrotetrazolate (DBX-1).

Certain aspects include where the second material is a detonating output material.

Certain aspects include where the detonating output material is a dry powder (dry explosive).

Certain aspects include where the detonating material includes pentaerythritol tetranitrate (PETN).

Certain aspects include where the wall segment includes stainless steel.

Certain aspects include where the body includes the wall segment.

Certain aspects include where a material of the wall segment is selected so that the wall segment does not rupture when the supersonic wave passes therethrough.

Certain aspects include where a thickness of the wall segment is selected so that the wall segment does not rupture when the supersonic wave passes therethrough.

Certain aspects include where the body includes a base and a cap. The cap is configured to secure to the base forming at least a portion of the receptacle therebetween.

Certain aspects include where the receptacle is further configured to receive at least a portion of the initiator module when the cap is not secured to the base. The receptacle is configured to secure the initiator module relative to the body when the cap is secured to the base.

Certain aspects include where the body includes an opening into the receptacle. The opening is sized and shaped for a portion of the initiator module to pass therethrough when the initiator module is coupled to the accelerator module.

Certain aspects include where the portion of the initiator module is at least one electrical pin.

Certain aspects include where the body includes an ejection tube (emitting tube) disposed on an opposite side of the wall segment from the receptacle. The ejection tube is aligned (arranged in line) with the propagation axis. The plurality of doped metal particles is disposed in the ejection tube.

Certain aspects include where the ejection tube is a straight cylinder, and wherein a cross-section of the ejection tube has a similar size to a cross-section of the receptacle.

Certain aspects include where the accelerator module is a component of a gene gun.

Certain aspects include where the first portion and the second portion are aligned (arranged in line) along the propagation axis.

Certain aspects include where the bottom surface is perpendicular to the propagation axis.

Certain aspects further include an adhesive disposed on at least a portion of the outer surface of the body. The plurality of doped metal particles is suspended in the adhesive.

Certain aspects further include a screen secured to the body in a position covering the plurality of doped metal particles and an adhesive disposed on the screen to prevent the plurality of doped metal particles from passing through the screen in the absence of the supersonic wave.

Certain aspects further include a seal. The receptacle is further configured to receive at least a portion of the initiator module. The seal is disposed in the receptacle to form a seal with the initiator module.

Certain aspects include where a particle of the plurality of doped metal particles has a diameter of about 1 micron.

Certain aspects include where the plurality of doped metal particles includes gold.

Certain aspects include where the plurality of doped metal particles includes tungsten.

Certain aspects include where the plurality of doped metal particles includes a chemical.

Certain aspects include where the chemical is DNA.

Certain aspects include where the initiator module is an electro explosive device (EED).

Certain aspects include where the electro explosive device (EED) includes an electrical input and a pyrotechnic output.

Certain aspects include where the pyrotechnic output is a mixture of zirconium and potassium perchlorate.

Certain aspects include where the electro explosive device (EED) includes a casing, wherein the pyrotechnic output is disposed in the casing.

Certain aspects include where the casing is metal.

An aspect is an accelerator module having a body with a propagation axis and defining (demarcating) a receptacle with a bottom surface. The propagation axis passes through the bottom surface. The accelerator module further includes a material disposed in the receptacle and configured to at least in part create a detonating (explosion) wave travelling at supersonic speed, a wall segment at least partially defined between the bottom surface of the receptacle and an outer surface of the body, the wall segment being sized to allow the detonating (explosion) wave to travel therethrough without rupturing the wall segment, and a plurality of doped metal particles disposed on the opposite side of the wall segment from the receptacle and generally aligned (arranged in line) with the propagation axis.

An aspect is a method for delivering a plurality of doped metal particles to cells within tissue using a portable device.

The method includes igniting a pyrotechnic charge disposed in the portable device to create a subsonic wave, the subsonic wave propagating along an axis towards a material disposed in the portable device, igniting the material with the subsonic wave to create a supersonic wave, the supersonic wave continuing to propagate along the axis towards a wall segment of the portable device, propagating the supersonic wave through the wall segment without rupturing the wall segment, and impinging the supersonic wave after passing through the wall segment on the plurality of doped metal particles to accelerate the plurality of doped metal particles to a speed.

Another aspect is a gene gun having a propagation axis extending at least between a pyrotechnic charge and a plurality of doped metal particles. The gene gun includes a deflagration-to-detonation transition material (DDT) disposed generally along the propagation axis, a detonating output material disposed on an opposite side of the DDT from the pyrotechnic charge and generally along the propagation axis, and a wall segment separating the detonating output material from the plurality of doped metal particles.

Advantageous Effects of Invention

According to the technique of this disclosure, in a device and a method for delivering a plurality of doped metal particles to cells, it is possible to provide a technique capable of increasing a speed of metal particles delivered to cells more than that in the conventional technique.

DESCRIPTION OF EMBODIMENTS

Figure 1:
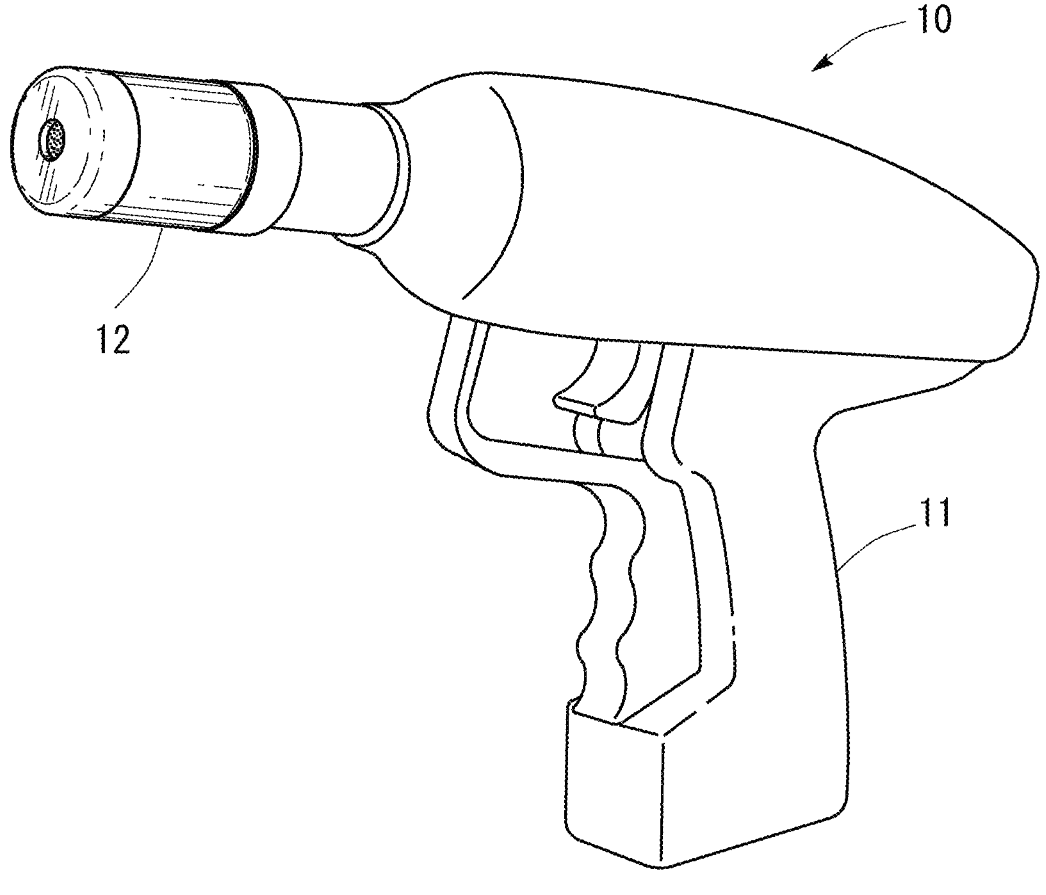
FIG. 1 is a perspective view of an embodiment of a gene gun that includes a handle and an accelerator module or cartridge according to a preferred embodiment of the present invention. The accelerator module is assembled to the handle and can be replaced after use.

Embodiments according to the present disclosure will be described below with reference to the drawings. Note that each of the configurations, combinations thereof, and the like in each embodiment is an example, and additions, omissions, substitutions, and other changes of the configuration may be made as appropriate without departing from the spirit of the present invention. The present disclosure is not limited by the embodiments and is limited only by the claims.

Examples of the particle delivery target to which the doped metal particles are delivered (introduced) in this disclosure include tissue, preferably, cells within tissue. When the particle delivery target is cells within tissue, the particle delivery target may be the nuclei or organelles in the cells.

Examples of the tissue include animal tissue and plant tissue. Examples of the animal include vertebrates, and specifically mammals (Mammalia), birds, reptiles, amphibians, and fishes. Examples of the plants include seed plants and spore plants, examples of the seed plants include angiosperms and gymnosperms, and examples of the spore plants include fern plants, moss plants and algae. When the tissue as the particle delivery target is animal tissues, examples thereof include epithelial tissues, connective tissues, muscle tissues, and nerve tissues; and further, for example, they may include organs, organs, epidermis (horny cell layers, intracutaneous), dermis, subcutaneous, muscles, and others. When the tissue as the particle delivery target is plant tissue, examples thereof may include meristems (such as apical meristems, cambium layers) and permanent tissue (such as epidermal tissue, conductive tissue, mechanical tissue, parenchyma), and others, and may also include, for example, roots, stems, leaves, and others.

The particle delivery target may be any one of an in vitro system, an in vivo system, and an ex vivo system. That is, the particle delivery target may be in a state of being present in an individual (living body), or may be in a state of being removed or separated from the individual (living body). That is, the latter is a state in which the particle delivery target is not present in the individual (living body), and when the particle delivery target is cells (preferably cells within tissue), specific examples of the cells (preferably, cells within tissue) may include an aspect excluding cells (preferably, cells within tissue) in a state of being present in an individual (living body). The individual (living body) may be an animal individual (living body) or a plant individual (living body), and aspects of the animals and the plants are as described above. When the individual (living body) is an animal individual (living body), this is preferably a vertebrate individual (living body), and more preferably a mammalian individual (living body). The mammals are not particularly limited, and examples thereof include humans and mammals other than humans. Examples of humans include able-bodied persons and persons suffering from diseases (patients), and the like. Examples of the mammals other than humans include mice, rats, guinea pigs, hamsters, cows, goats, sheep, pigs, monkeys, dogs, cats, and others.

The accelerator module related to this disclosure is configured to include: a receptacle with a propagation axis; a material disposed in the receptacle and triggered by a subsonic wave created by an initiator module so as to create a supersonic wave; and a wall segment extending through the propagation axis and separating the inside and outside of the receptacle, the outer surface of the wall segment on which a plurality of doped metal particles being able to be disposed to be aligned along the propagation axis, the supersonic wave created by the material creating a supersonic wave propagates through the wall segment and after passing therethrough, impinges on the metal particles, to thereby accelerate the plurality of doped metal particles. The initiator module has, for example, a pyrotechnic charge (powder), and operates with supply of operating power to cause the pyrotechnic charge to ignite and burn, to thereby create deflagration, which is a subsonic wave. The deflagration which is the subsonic wave created by the initiator module propagates along the propagation axis towards the material creating a supersonic wave contained in the receptacle, so that the material is ignited by the deflagration, which is the subsonic wave created by the material. When the material creating a supersonic wave is ignited, a detonating (explosion) wave which is a supersonic wave is created, and the detonating wave which is the supersonic wave travels through the wall segment along the propagation axis. The detonating wave (supersonic wave) having reached the wall segment then reaches the outer surface of the wall segment while propagating (passing) through the inside of the solid wall segment, and impinging on the plurality of doped metal particles disposed on the outer surface. As a result, the metal particles are provided with acceleration energy from the detonating wave (supersonic wave), and the metal particles are ejected at a high speed, to reach the above the particle delivery target.

The pyrotechnic charge of the initiator module may be, for example, zirconium or potassium perchlorate, or a mixture thereof. Of course, the pyrotechnic charge is not limited to these, and various types of powder (explosive) can be used as far as they can create deflagration which is a subsonic wave through ignition and combustion thereof. For example, a pyrotechnic charge used in an initiator used for inflating an airbag for an automobile is suitably applicable to the pyrotechnic charge according to this disclosure.

The material creating a supersonic wave by being ignited by a subsonic wave is not particularly limited, but various type of dry powders can be suitably adopted. The material creating a supersonic wave by being ignited by a subsonic wave can be considered as a material for transitioning deflagration to detonation. Examples of the material creating a supersonic wave by being ignited by a subsonic wave preferably include, for example, lead azide, copper (I) 5-nitrotetrazolate (DBX-1), pentaerythritol tetranitrate (PETN), and others. Of course, they are not limited to these, and various types of explosives can be adopted. The receptacle of the accelerator module can contain plural types of materials creating the above supersonic wave. For example, the material creating a supersonic wave by being ignited by a subsonic wave may include the first material and the second material, and they may be disposed in the receptacle so as to be aligned along the propagation axis. The first material and the second material may be heterogeneous explosive materials or homologous explosive materials.

The wall segment of the accelerator module allows solid propagation of the detonating wave as the supersonic wave created in the receptacle. Here, a speed of sound is referred to as a speed of sound propagating through a material (medium), and differs depending on the medium, and the speed of sound can be significantly increased when a solid is used as a medium compared with the case in which a gas is used as a medium. For example, a speed of sound in stainless steel is several times higher than a speed of sound in helium gas. Of course, the material used for the wall segment is not limited to stainless steel. The wall segment may be formed of, for example, aluminum or other metal, or may be formed of a material other than metal. The wall segment thus formed can further accelerates a detonating wave as a supersonic wave having entered along the propagation axis through the solid propagation, for example. The supersonic wave (detonating wave) having reached the outer surface of the wall segment is caused to impinge on the metal particles, to thereby eject the metal particles at a supersonic speed, for example. In this manner, the accelerator module and the gene gun provided therewith according to this disclosure increase the ejection speed of the metal particles as compared with that in the conventional art, to thereby provide an accelerator module or a gene gun having a higher practicability.

FIG. 1 is a perspective view of an embodiment of a gene gun 10 that includes a handle 11 and an accelerator module or cartridge 12 according to a preferred embodiment of the present invention. The accelerator module 12 is assembled to the handle 11 and can be replaced after use. Certain embodiments of the gene gun 10 can be used in a laboratory or medical facility for implanting DNA into cell nuclei. The cell nuclei could be of either plants or animals. For example, the cell nuclei can be of a patient (human).

In certain embodiments, the accelerator module 12 includes a body 14 and an initiator 30. In certain embodiments, the initiator 30 is assembled to the body 14. For example, in certain embodiments, the body 14 demarcates (defines) a receptacle (most clearly illustrated in FIG. 8) sized and shaped to receive at least a portion of the initiator 30. In certain embodiments, the body 14 and the initiator 30 are separately assembled to a frame. The frame is configured to fix a position of the body 14 relative to a position of the initiator 30.

In certain embodiments, at least a portion of the body 14 includes a material selected based at least in part on the strength of the material. In certain embodiments, the material is selected so that the body 14 can contain forces caused by a detonation occurring within the body 14. In this way, the material exhibits sufficient strength to contain the forces of detonation within the body 14. In certain embodiments, at least a portion of the body 14 includes a metal. Of course, the body 14 need not include metal and instead can include materials other than metal, or a combination of materials. For example, in certain embodiments, the body 14 includes a plurality of materials.

Figure 2:
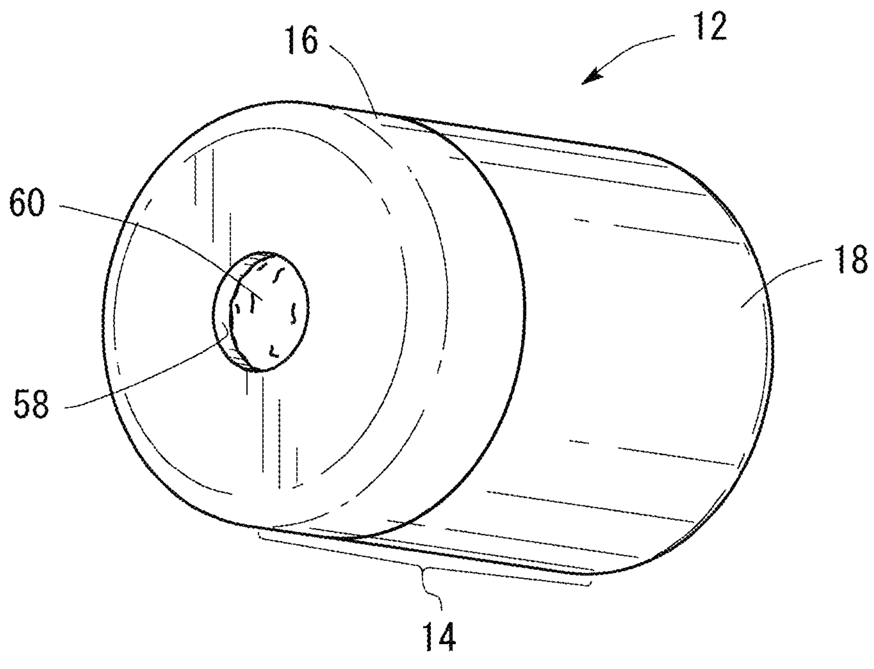
FIG. 2 is a perspective view of a distal end of the accelerator module from FIG. 1 illustrating an ejection tube including a plurality of particles.

FIG. 2 is a perspective view of a distal end of the body 14 of the accelerator module 12 from FIG. 1 illustrating an ejection tube (emitting tube) 58 including a plurality of particles 60. In certain embodiments, the plurality of particles 60 are doped metal particles. In certain embodiments, the plurality of particles 60 are free to travel unimpeded to the tissue.

Figure 8:
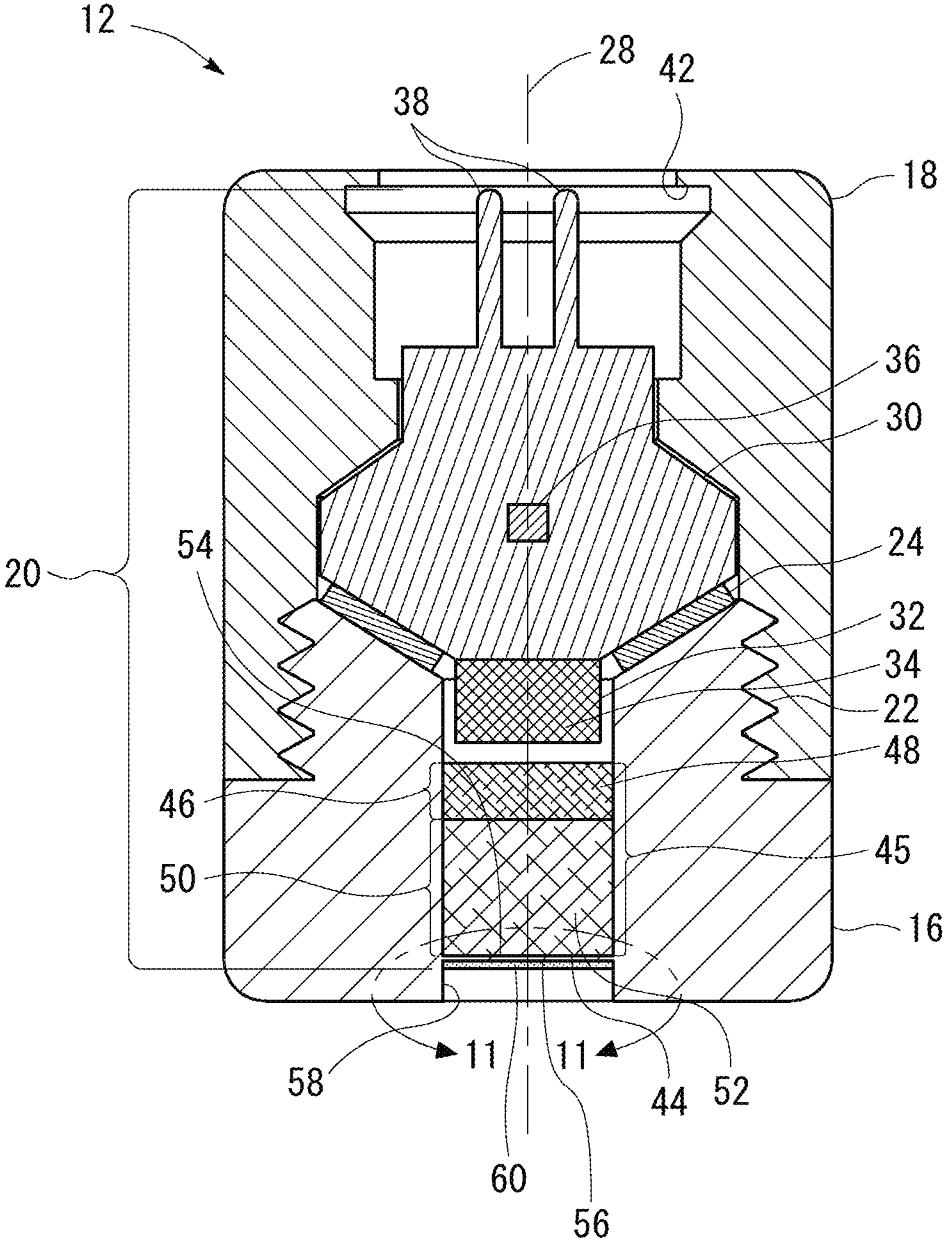
FIG. 8 is a cross-sectional view through the accelerator module of FIG. 4, as viewed along the cut-plane 8-8 of FIG. 4, illustrating both the initiator and the chamber aligned along an axis and with the ejection tube. A wall segment separates the chamber from the ejection tube.

In certain embodiments, the body 14 includes a wall segment 44 (most clearly illustrated in FIG. 8). In certain embodiments, the wall segment 44 is a part of the body 14 which separates the receptacle 20 from the plurality of particles 60. In certain embodiments, the gene gun 10 creates a detonating (explosion) wave that travels through the wall segment 44 of the accelerator module 12 but does not rupture the wall segment 44.

In certain embodiments, the wall segment 44 does not rupture when the detonating wave passes therethrough and thus maintains a barrier between the detonation (explosive) material and the tissue. In certain embodiments, the wall segment 44 of the body 14 ruptures when the plurality of particles 60 is ejected (emitted) from the ejection tube 58 but, due to for example, the size and shape of the rupture attenuates any loss in pressure from the gene gun 10 sufficiently so that the plurality of particles 60 still have an initial velocity that is greater than the speed of sound before entering the tissue.

The detonating wave (explosion wave) travels though the wall segment 44 at the speed of sound in the wall material before exiting the wall segment 44 (being ejected from the wall segment 44). The exiting detonating wave (explosion wave) contacts and accelerates the plurality of particles 60 to an initial speed similar to the speed of the detonating wave (explosion wave) as the detonating wave (explosion wave) passed through the wall segment 44. By passing the detonating wave (explosion wave) through the wall segment 44 as opposed through a gas, the speed of the detonating wave (explosion wave) increases to a value greater than the speed of sound through the gas.

In certain embodiments, at least a portion of the body 14 of the accelerator module 12 includes a material that has a high speed of sound (a material whose speed of sound is high). In certain embodiments, the greater (faster, higher) the speed of sound is through the material increases an initial velocity of the plurality of particles 60 exiting the ejection tube 58.

In certain embodiments, the wall segment 44 has a thickness of 1 mm. In certain embodiments, the wall segment 44 has a thickness of 0.5 mm. In certain embodiments, the wall segment 44 has a thickness of 2 mm. In certain embodiments, the wall segment 44 has a varying or non-uniform wall thickness. The disclosure is not limited to the recited values and includes any other values for thickness. In certain embodiments, a material of the wall segment 44 is selected based at least in part on the speed of sound through the wall segment 44. In certain embodiments, the material of the wall segment 44 is selected so that the body 14 can accelerate the plurality of particles 60 to a sufficient initial velocity that causes the plurality of particles 60 to penetrate the tissue to a desired depth. In this way, the material of the wall segment 44 exhibits a sufficient speed of sound for the plurality of particles 60 to reach the desired depth in the tissue. In certain embodiments, a first portion of the body 14 includes a material that has a sufficient strength to contain the forces of detonation while a second portion of the same body 14 includes a material that has a sufficient speed of sound to accelerate the plurality of particles 60 to a sufficient speed of sound for the plurality of particles 60 to reach the desired depth in the tissue.

Figure 3:
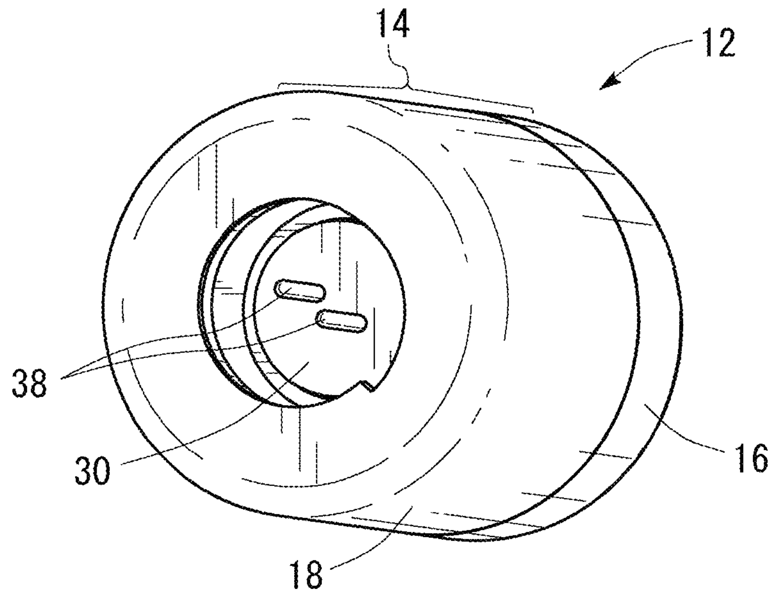
FIG. 3 is a perspective view of a proximal end of the accelerator module from FIG. 1 illustrating at least one pin of an initiator for electrically coupling the accelerator module to the handle.

FIG. 3 is a perspective view of a proximal end of the accelerator module 12 from FIG. 1 illustrating at least one pin 38 (electrical input) of the initiator 30 for electrically coupling the accelerator module 12 to the handle 11. In certain embodiments, the accelerator module 12 is incorporated into the gene gun 10 by any means desired. As will be explained below, in certain embodiments, an electrical firing mechanism, such as the initiator 30, is employed to provide a firing pulse at a desired time.

Figure 4:
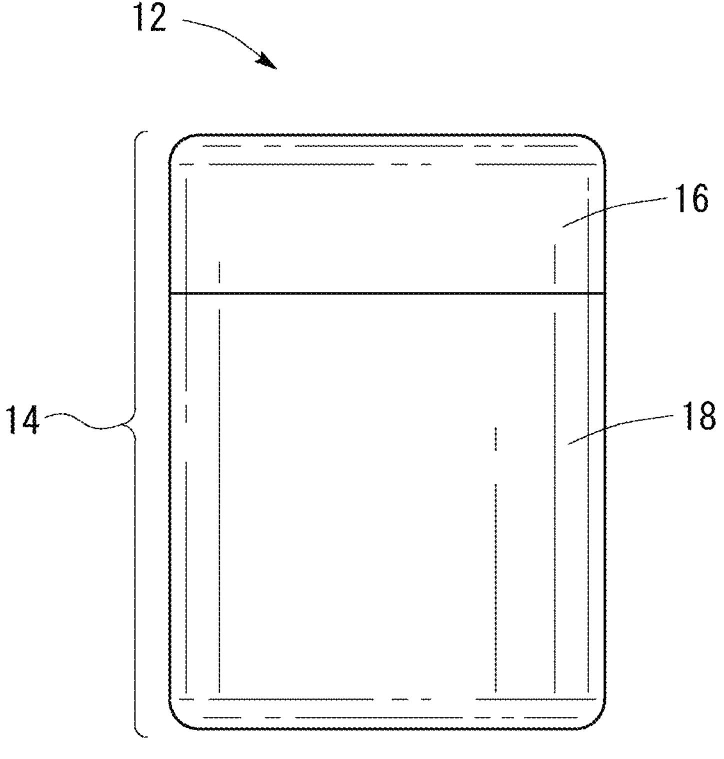
FIG. 4 is a side view of the accelerator module from FIG. 2 illustrating a cap and a base of the accelerator module secured together forming a receptacle. The receptacle receives at least a portion of the initiator as well as demarcates (specifies) a chamber.

FIG. 4 is a side view of the accelerator module 12 from FIG. 2. In the illustrated embodiment, the body 14 of the accelerator module 12 includes a base 16 and a cap 18. In other embodiments, the body 14 is manufactured as a single monolithic structure. In other embodiments, the body 14 of the accelerator module 12 is assembled from more than two structures.

In certain embodiments, the base 16 and the cap 18 include a complementary engagement structure 22. The engagement structure 22 is configured to secure the base 16 and the cap 18 together. In certain embodiments, the engagement structure 22 includes one or more of a weld, an adhesive, a fastener, a mechanical lock, a thread, or any other structure by which the base 16 can be secured to the cap 18. In other embodiments, a frame is employed to secure the base 16 relative to the cap 18 without directly securing together the base 16 and the cap 18.

Figure 5:
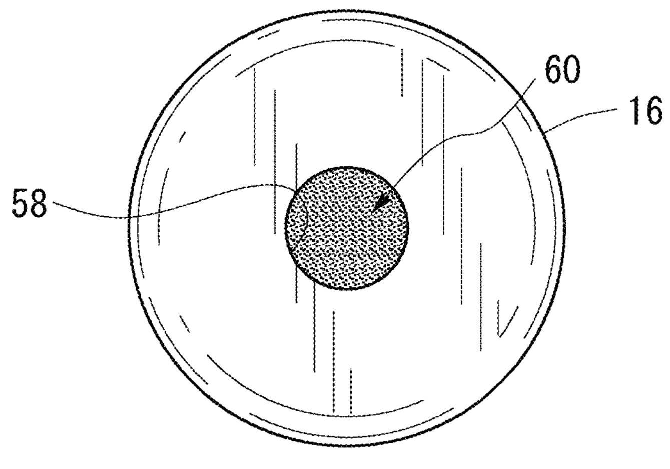
FIG. 5 is a plan view of the distal end of the accelerator module from FIG. 2 illustrating the plurality of particles disposed in the ejection tube.

FIG. 5 is a plan view of the distal end of the accelerator module 12 from FIG. 2 illustrating the plurality of particles 60 disposed against an outer surface 56 (most clearly illustrated in FIG. 8) of the body 14. In certain embodiments, the outer surface 56 is a portion of a concave shape within the body 14. In certain embodiments, the concave shape has the form of the ejection tube (emitting tube) 58. In certain embodiments, the plurality of particles 60 are supported by at least the outer surface 56 of the ejection tube 58. In certain embodiments at least a portion of the bore forming the tubular wall of the ejection tube 58 supports the plurality of particles 60.

In certain embodiments, the outer surface 56 is not a portion of a concave shape and instead is part of a convex shape against which the plurality of particles 60 are disposed. In certain embodiments, the outer surface 56 against which the plurality of particles 60 is disposed has a planar shape.

In certain embodiments, the plurality of particles 60 are attached to at least the outer surface 56. In certain embodiments, the plurality of particles 60 are arranged on the outer surface 56. In certain embodiments, the plurality of particles 60 form stacks (is layered) on the outer surface 56. In certain embodiments, the plurality of particles 60 are randomly arranged on the outer surface 56.

In certain embodiments, the plurality of particles 60 are metal particles. In certain embodiments, the plurality of particles 60 include small metal particles. In certain embodiments, each particle of the plurality of particles 60 are on the order of 1 micron in size. In certain embodiments, each particle of the plurality of particles 60 are on the order of 2 microns in size. Of course, the size of the particles of the plurality of particles 60 is not so limited and can have other sizes.

In certain embodiments, the particles of the plurality of particles 60 have aspherical shape. In other embodiments, the particles of the plurality of particles 60 have a conical shape. In other embodiments, the particles of the plurality of particles 60 have a cylindrical shape. In other embodiments, the particles of the plurality of particles 60 have a cube shape. In other embodiments, the particles of the plurality of particles 60 have a mix of more than one shape.

In certain embodiments, the particles of the plurality of particles 60 are homogenous. In certain embodiments, at least some of the particles of the plurality of particles 60 are distinct in size and shape from some other particles.

In certain embodiments, the plurality of particles 60 are made of a dense material. For example, in certain embodiments, the dense material is gold, tungsten, or other known dense materials. In certain embodiments, it may desirable that the plurality of particles 60 include a high density which increases kinetic energy of the plurality of particles 60 over particles that have a lower density when accelerated to the same velocity.

In certain embodiments, the plurality of particles 60 are doped. In certain embodiments, chemicals are attached to the particle. In certain embodiments, the plurality of particles 60 are coated with the chemical. In certain embodiments, the chemicals include DNA. In certain embodiments, the DNA is plasmid DNA. In certain embodiments, the DNA is a circular, double-stranded DNA molecule. In certain embodiments, the doped plurality of particles 60 are subcellular-sized particles coated with DNA. In certain embodiments, the DNA is chromosomal DNA.

In certain embodiments, the ejection tube 58 can output the plurality of particles 60 in a predetermined direction. For example, the ejection tube 58 can output the plurality of particles 60 along an axis 28. In certain embodiments, the axis 28 is a propagation axis. In some embodiments, the ejection tube 58 can direct the plurality of particles 60 towards a predetermined location on the tissue.

In certain embodiments, the ejection tube 58 has a constant internal diameter. In certain embodiments, the ejection tube 58 has a converging internal diameter in a direction of ejection. In certain embodiments, the ejection tube 58 has a diverging internal diameter in the direction of ejection (direction of injection). In certain embodiments, the ejection tube 58 has converging and then diverging internal diameters in the direction of ejection.

In certain embodiments, the ejection tube 58 can have one or more vanes formed in an inner wall of the bore of ejection tube 58. In certain embodiments, the one or more vanes are sized and shaped to straighten the plurality of particles 60 being ejected from the gene gun 10. The vanes can reduce turbulence in the plurality of particles 60 as the plurality of particles 60 is ejected from the ejection tube 58.

In certain embodiments, the gene gun 10 ejects the doped plurality of particles 60 into tissues, cells and/or organelles. In certain embodiments, the ejection of the doped plurality of particles 60 is performed in vitro (outside a body). In certain other embodiments, the ejection of the doped plurality of particles 60 is performed in vivo (inside a body). In certain embodiments, the gene gun 10 ejects the doped plurality of particles 60 into cell nuclei.

When ejected, the plurality of particles 60 desirably penetrate the tissue. In certain embodiments, the plurality of particles 60 ejected by the gene gun 10 penetrate the tissue to a desired depth into the tissue. In certain embodiments, the desired depth is predefined. In certain embodiments, the desired depth is determined at least in part based on the composition (configuration) of the plurality of particles 60. For example, the desired depth can be different for each different accelerator module 12.

Figure 6:
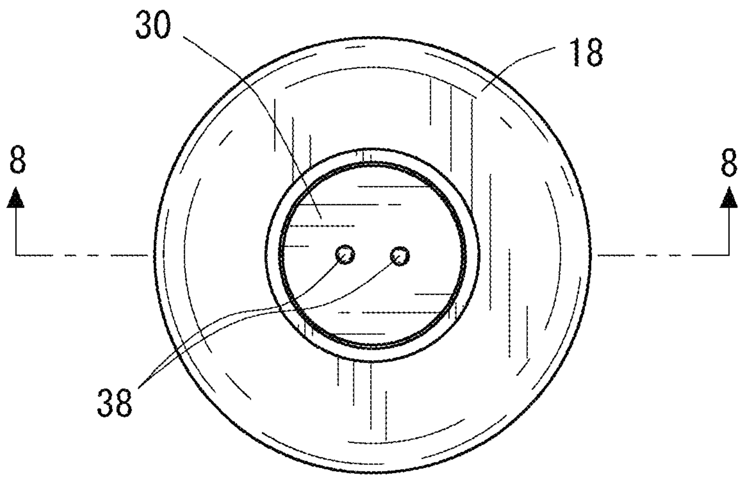
FIG. 6 is a plan view of the proximal end of the accelerator module from FIG. 2 illustrating the at least one pin configured for connecting to a connector of the handle.

FIG. 6 is a plan view of the proximal end of the accelerator module 12 from FIG. 2 illustrating the at least one pin 38 of the initiator 30 configured for connecting to a connector 40 of the handle 11. In certain embodiments, the at least one pin 38 includes two electrically conductive pins. In certain embodiments, the two electrically conductive pins are gold-plated. In certain embodiments, the at least one pin 38 of the initiator 30 electrically mates with the connector 40.

In certain embodiments, the initiator 30 is fired by an electrical input. In certain embodiments, the at least one pin 38 receives the electrical input in the form of an electrical firing pulse. In certain embodiments, the gene gun 10 includes one or more electronic components for triggering the initiator 30. In certain embodiments, the one or more electronic components are supported by the gene gun 10.

In certain embodiments, the one or more electronic components are configured to generate an electric current to trigger the initiator 30. In certain embodiments, the one or more electronic components include a controller. In certain embodiments, the gene gun 10 includes an interface for a user to initiate the one or more electronic components to trigger the initiator 30. In certain embodiments, the interface is a pull trigger.

In certain embodiments, the gene gun 10 includes an energy source for the one or more electronic components. In certain embodiments, the energy source is supported by the handle 11. In certain embodiments, the energy source can be a battery. In certain embodiments, the battery powers the one or more electronic components to fire the initiator 30.

In certain embodiments, the battery or other source of electrical energy provides the electrical firing pulse to the initiator 30 via the connector 40. In certain embodiments, a magnitude and a duration of the electrical firing pulse applied to the initiator 30 is 1.2 amps and 2 ms. In certain embodiments, the magnitude and the duration of the electrical firing pulse applied to the initiator 30 is 1.75 amps and 0.5 ms. The disclosure is not limited to the recited values and includes any other values for magnitude and duration. In certain embodiments, the magnitude and the duration of the electrical firing pulse applied to the initiator 30 are selected based at least in part on the operational characteristics of the initiator 30.

Figure 7:
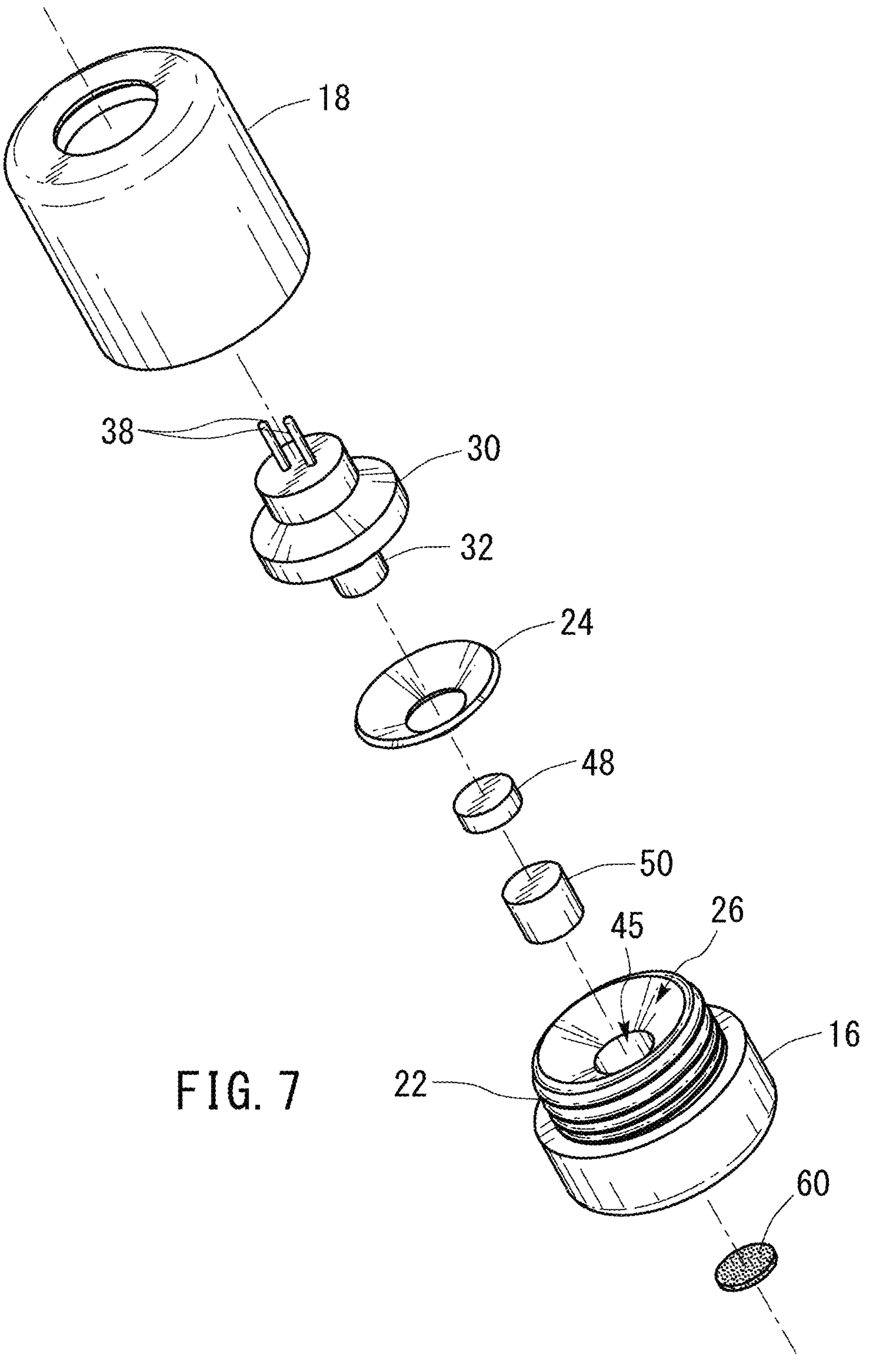
FIG. 7 is a perspective exploded view of the accelerator module from FIG. 2 illustrating, for example, the initiator separates from the receptacle.

FIG. 7 is a perspective exploded view of the accelerator module 12 from FIG. 2 illustrating, for example, the initiator 30 separate from the receptacle 20. In certain embodiments, the initiator 30 can be any electro explosive device (EED). In certain embodiments, the initiator 30 includes a pyrotechnic charge 34 (pyrotechnic output). The pyrotechnic charge 34 is configured to create a conflagration when ignited. In certain embodiments, the initiator 30 includes a casing 32. In certain embodiments, the casing 32 includes the pyrotechnic charge 34. In certain embodiments, the initiator 30 is an automotive initiator. Examples of automotive initiators include initiators used for car airbags.

In certain embodiments, the receptacle 20 is formed by the base 16 and the cap 18. In certain embodiments, the base 16 includes at least a portion of the receptacle 20. In certain embodiments, the cap 18 includes at least a portion of the receptacle 20. In certain embodiments, at least a portion of the initiator 30 is disposed in the receptacle 20. In certain embodiments, the base 16 and the cap 18 are secured together forming the receptacle. In certain embodiments, the base 16 and the cap 18 are secured together after the initiator 30 is placed within the receptacle 20.

In certain embodiments, the receptacle 20 is sized and shaped relative to the size and shape of the initiator 30 so as to prevent movement of the initiator 30 relative to the receptacle 20 when the cap 18 is secured to the base 16. In this way, the initiator 30 can be locked (fixed) within the receptacle 20 at least when the base 16 and cap 18 are secured together.

FIG. 8 is a cross-sectional view through the accelerator module 12 of FIG. 4, as viewed along the cut-plane 8-8 of FIG. 4, illustrating both the initiator 30 and a chamber 45 aligned (arranged in line) along the axis 28 and with the ejection tube 58. In certain embodiments, the chamber 45 is a portion of the receptacle 20 that is disposed between the initiator 30 and a bottom surface 54 of the receptacle 20. The wall segment 44 separates the chamber 45 from the ejection tube 58.

In certain embodiments, the connector 40 is structurally secured to the body 14. In certain embodiments, the body 14 includes a lip 42 configured to capture a portion of the connector 40 to structurally secure the connector 40 to the body 14. In certain embodiments, the user can separate or decouple the connector 40 from the body 14. For example, after use of the accelerator module 12, the connector 40 can be decoupled from the body 14 allowing a spent accelerator module 12 to be removed and replaced with a new accelerator module 12.

In certain embodiments, the receptacle 20 includes an opening 26. In certain embodiments, the opening 26 is disposed in the base 16. In certain embodiments, the opening 26 is disposed between a surface of the initiator 30 and a surface of the base 16. In certain embodiments, at least a portion of the initiator 30 passes through the opening 26 in the base 16 before the cap 18 is secured to the base 16 forming the complete receptacle 20.

In certain embodiments, the initiator 30 includes a resistance element 36. In certain embodiments, the resistance element 36 is disposed relative to the casing 32. In certain embodiments, the electrical firing pulse applied to the initiator 30 heats up the resistance element 36 within the initiator 30. In certain embodiments, the resistance element 36 is sufficiently heated by the electrical firing pulse to ignite the pyrotechnic charge 34 within the casing 32. In certain embodiments, the pyrotechnic charge 34 is a mixture of zirconium and potassium perchlorate. In certain embodiments, the pyrotechnic charge 34 is a single material or a mixture of other materials.

In certain embodiments, the casing 32 is made of metal. In certain embodiments, the metal is stainless steel. Of course, the casing 32 can be made of any other metal in addition to stainless steel. In certain embodiments, the metal is aluminum. In certain embodiments, the casing 32 is made of a polymer. In certain embodiments, the material and thickness of the casing 32 is selected so that the material ruptures in response to the pyrotechnic charge 34 being ignited. The rupture in the casing 32 allows the conflagration to escape the casing 32 and travel or propagate at a subsonic speed along the axis 28 towards the chamber 45.

In certain embodiments, the conflagration escaping from the casing 32 ignites material in the chamber 45. Once the pyrotechnic charge 34 is triggered, the pressure released by the pyrotechnic charge 34 in the casing 32 breaks the casing 32 allowing the deflagration to propagate at subsonic speed along the axis 28 and ignite material in the chamber 45.

In certain embodiments, the accelerator module 12 includes a seal 24. In certain embodiments, the seal 24 is a gasket, O-ring, or other suitable structure. In certain embodiments, the seal 24 is disposed between one or more surfaces of the body 14 and one or more surfaces of the initiator 30. In certain embodiments, the seal 24 is disposed in the opening 26. In certain embodiments, the seal 24 inhibits the conflagration escaping from the casing 32 from leaking through the opening 26 back towards the connector 40 when the initiator 30 is ignited. In certain embodiments, the seal 24 inhibits the detonated material in the chamber 45 from leaking through the opening 26 back towards the connector 40 when ignited by the conflagration escaping from the casing 32 through the rupture.

In certain embodiments, the material in the chamber 45 is selected to create a detonating (explosion) wave when the material is ignited by the conflagration caused by ignition of the pyrotechnic charge 34. In certain embodiments, the detonating (explosion) wave travels at a speed that is greater than the speed of sound.

In certain embodiments, to achieve the desired detonating (explosion) wave from the chamber 45, the speed of the entire pyrotechnic reaction, which is initially a subsonic deflagration caused by ignition of the pyrotechnic charge 34, is increased to greater than the speed of sound by the detonation of the material in the chamber 45. In certain embodiments, one or more materials are disposed in the chamber 45 to create the desired detonating (explosion) wave.

For example, in certain embodiments, the material includes a deflagration-to-detonation transition (DDT) material and a detonating output material. In certain embodiments, each of the materials is disposed in at least a portion of the chamber 45. In certain embodiments, the material is one or more of lead azide, copper (I) 5-nitrotetrazolate (DBX-1), and pentaerythritol tetranitrate (PETN). Of course, the disclosure is not limited to the listed materials or combinations of materials and other materials or combinations of materials may be employed that create the desired detonating (explosion) wave.

In certain embodiments, the material includes at least a first material 48 and a second material 52. The first material 48 and the second material 52 may be disposed in a first portion 46 and a second portion 50 of the chamber 45, respectively. In certain embodiments, the first material 48 is separated from the second material 52 in the chamber 45. In certain embodiments, the first material 48 contacts the second material 52 at an interface. In certain embodiments, the first material 48 is separated from the second material 52 by a barrier. In certain embodiments, the barrier is a transitory barrier between the first material 48 and the second material 52. For example, once the first material 48 is ignited, the barrier ruptures. In certain embodiments, the first material 48 is disposed around an outer periphery of the second material 52. In certain embodiments, the first material 48 and the second material 52 form a mixture within the chamber 45.

In certain embodiments, the interface between the first material 48 and the second material 52 is arranged normal to the axis 28. In certain embodiments, the position of the interface promotes propagation of the detonating (explosion) wave along the axis 28 towards the wall segment 44. In certain embodiments, the interface is not arranged normal to the axis 28. In certain embodiments, a size of a contact area between the first material 48 and the second material 52 is selected to promote detonation of the second material 52 by the first material 48. In certain embodiments, the interface can be smooth. In certain embodiments, the interface can be bumpy.

In the illustrated embodiments, the first portion 46 is disposed closer to the initiator 30 than the second portion 50. In the illustrated embodiment, the second portion 50 is disposed between the first portion 46 and the wall segment 44.

In certain embodiments, a ratio of the first material 48 to the second material 52 is 50/50. Of course, other ratios are within the scope of this disclosure. For example, in certain embodiments, the ratio of the first material 48 to the second material 52 is 40/60. For example, in certain embodiments, the ratio of the first material 48 to the second material 52 is 60/40.

In certain embodiments, the first material 48 is a deflagration-to-detonation transition (DDT) material. In certain embodiments, the first material 48 is a dry powder. In certain embodiments, the first material 48 is the lead azide material. In certain embodiments, the first material 48 is the copper (I) 5-nitrotetrazolate (DBX-1) material.

In certain embodiments, the second material 52 is a detonating output material. In certain embodiments, the second material 52 is a dry powder. In certain embodiments, the second material 52 is pentaerythritol tetranitrate (PETN). In certain embodiments, the detonating wave produced by the PETN travels at greater than the speed of sound. In certain embodiments, the detonating (explosion) wave produced by the PETN produces a similar detonating (explosion) wave in the wall segment 44.

In certain embodiments, the detonating (explosion) wave continues through the wall segment 44 and imparts its velocity to the plurality of particles 60 disposed against the outer surface 56 on the body 14. The detonating (explosion) wave then ejects (emits) the plurality of particles 60 from the body 14 at an initial speed that exceeds the speed of sound. In certain embodiments, the plurality of particles 60 are ejected at an initial velocity that is the same as the velocity of the detonating (explosion) wave passing through the wall segment 44.

Figure 9:
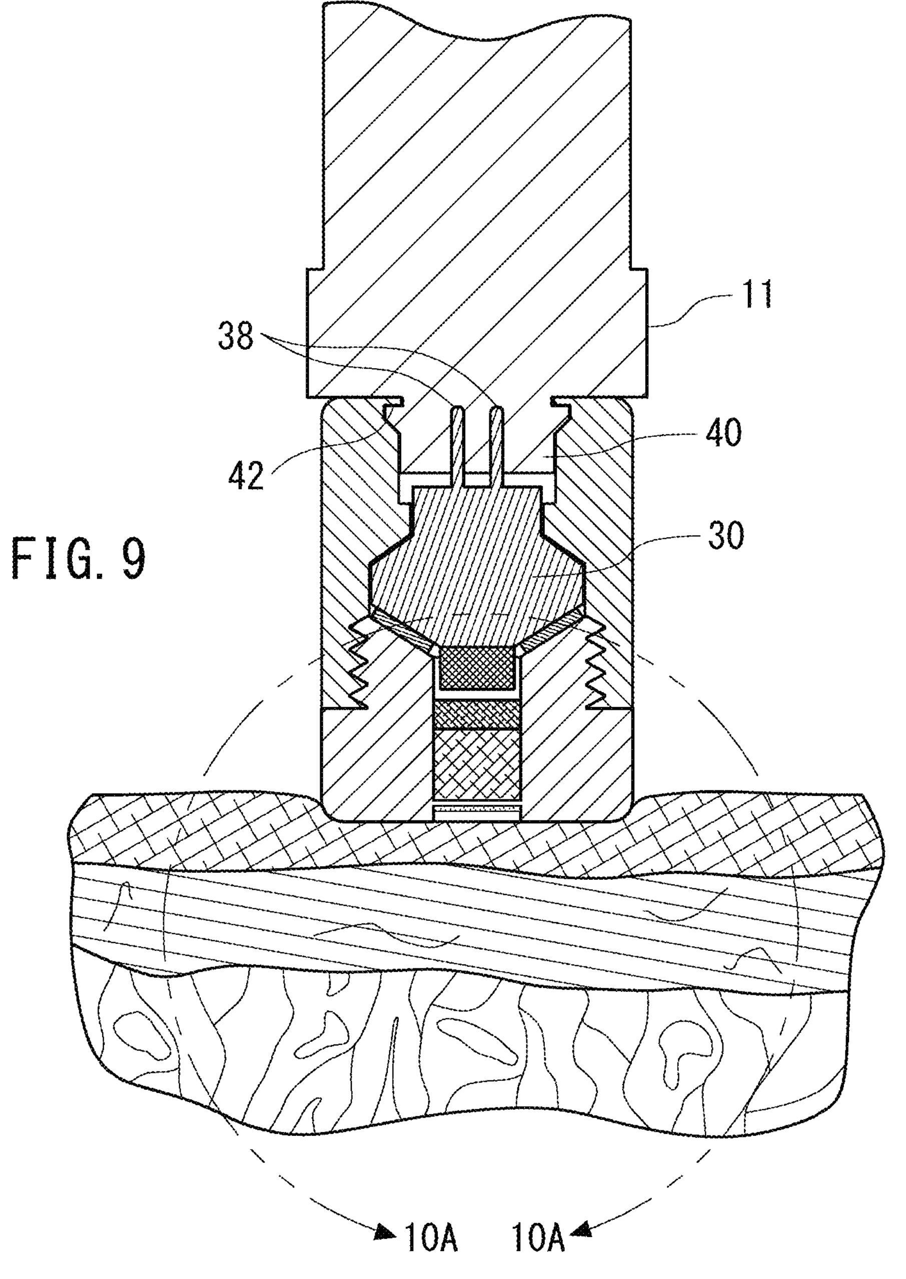
FIG. 9 is a cross-sectional view similar to FIG. 8 except that at least one pin is connected to the connector of the handle and the distal end of the accelerator module has been placed against tissue.
Figure 10A:
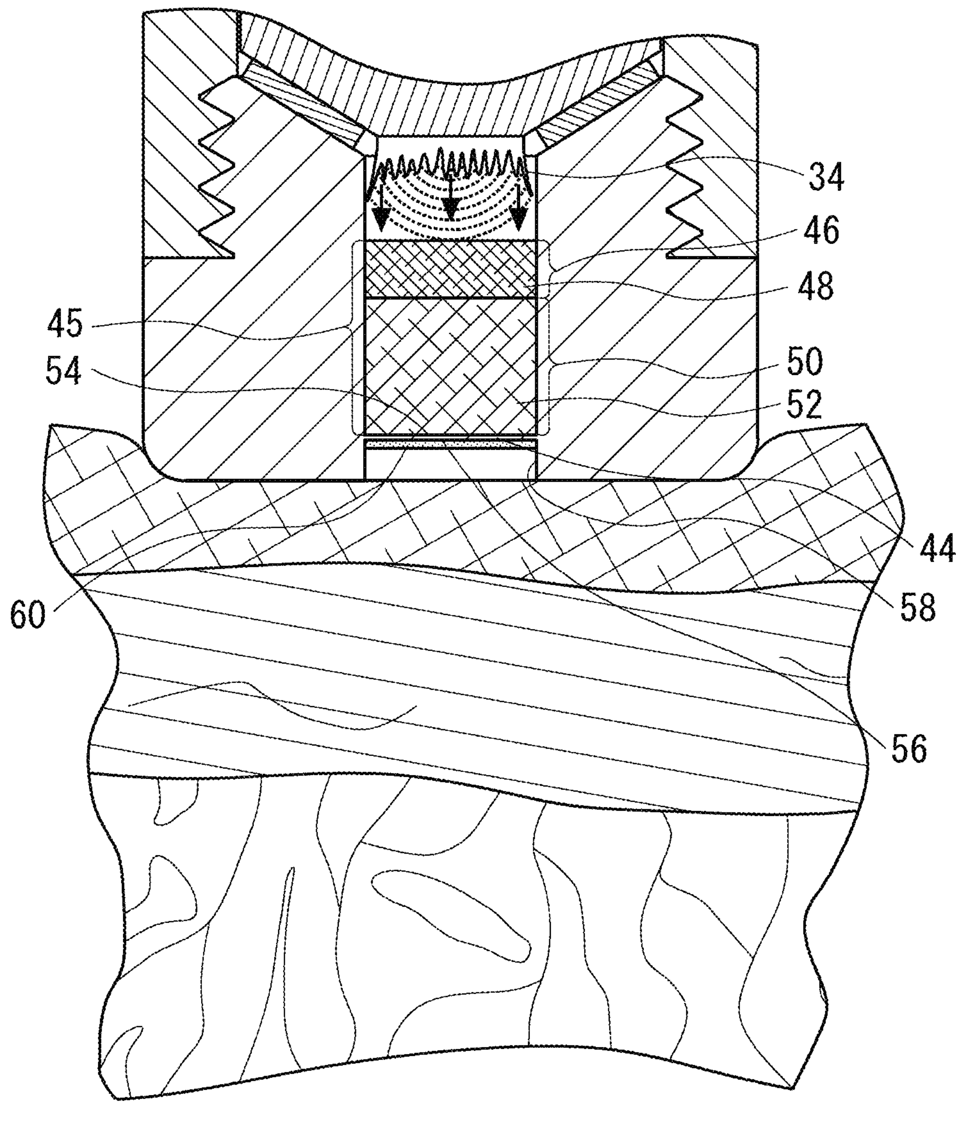
FIG. 10A is a partial cross-sectional view similar to FIG. 9 except illustrating steps of the accelerator module being ignited causing a supersonic shockwave to pass through the wall segment and accelerate the plurality of particles to exit the ejection tube and pass through the tissue.
Figure 10B:
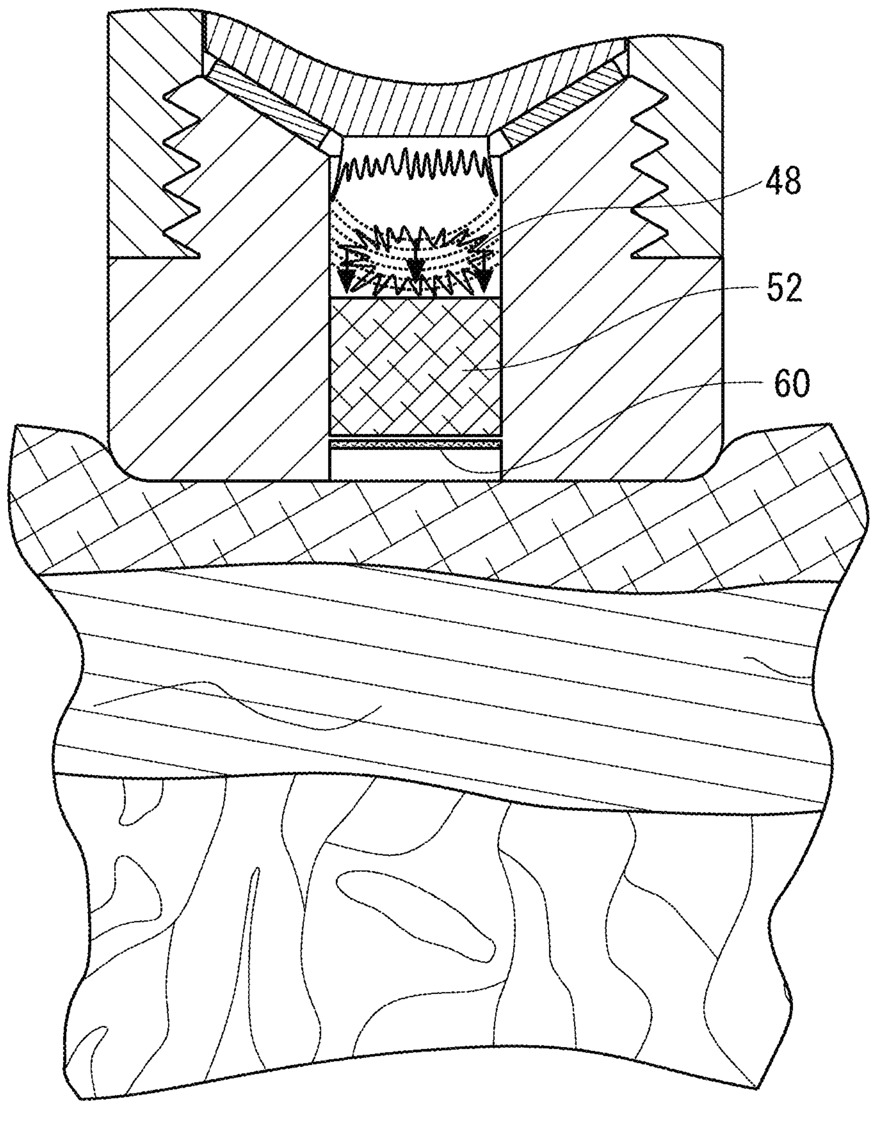
FIG. 10B is a partial cross-sectional view similar to FIG. 9 except illustrating steps of the accelerator module being ignited causing a supersonic shockwave to pass through the wall segment and accelerate the plurality of particles to exit the ejection tube and pass through the tissue.
Figure 10C:
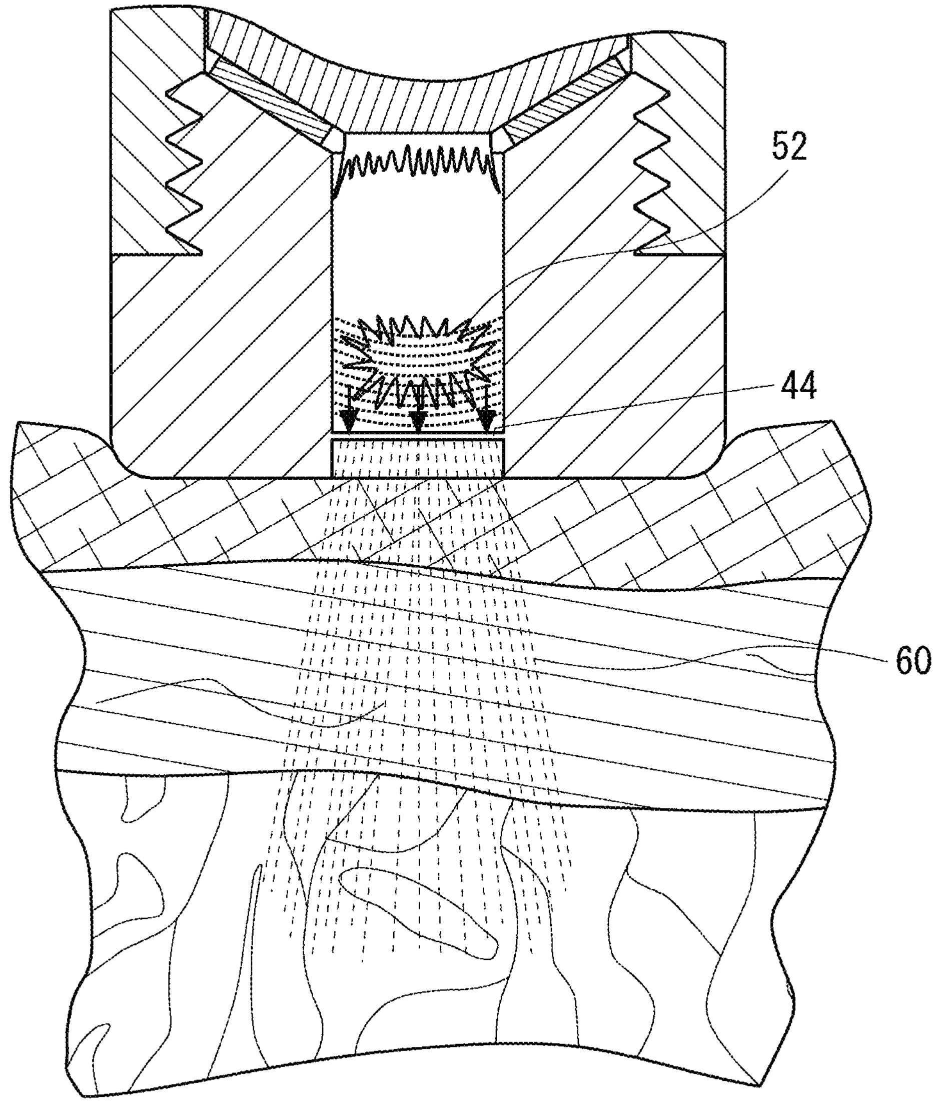
FIG. 10C is a partial cross-sectional view similar to FIG. 9 except illustrating steps of the accelerator module being ignited causing a supersonic shockwave to pass through the wall segment and accelerate the plurality of particles to exit the ejection tube and pass through the tissue.

FIG. 9 is a cross-sectional view similar to FIG. 8 except the at least one pin 38 is connected to the connector 40 of the handle 11 and the distal end of the accelerator module 12 has been placed against tissue. FIGS. 10A-C are partial cross-sectional views similar to FIG. 9 except illustrating steps of the accelerator module 12 being ignited causing a supersonic shockwave to pass through the wall segment 44 and accelerate the plurality of particles 60 to exit the ejection tube 58 and pass through the tissue.

FIG. 10A illustrates the initiator 30 being fired (ignited) by the electrical input. In certain embodiments, the at least one pin 38 receives the electrical input in the form of an electrical firing pulse. The initiator 30 includes the pyrotechnic charge 34. The pyrotechnic charge 34 creates the conflagration when ignited. Once the pyrotechnic charge 34 is triggered, the pressure released by the pyrotechnic charge 34 in the casing 32 breaks the casing 32 allowing the deflagration to propagate at subsonic speed along the axis 28 towards the first material 48 in the chamber 45. The deflagration caused by the pyrotechnic charge 34 creates a propagating subsonic flame. In this way, the subsonic flame moves towards the chamber 45.

FIG. 10B illustrates the escaping conflagration igniting the first material 48 in the chamber 45. In certain embodiments, the first material 48 is a deflagration-to-detonation transition (DDT) material. Once ignited, the first material 48 transitions (shifts) from deflagration to detonation (explosion). While the first material 48 is ignited by the subsonic flame, the subsonic flame eventually transitions to a detonation (explosion). In this way, the subsonic flame entering the first material 48 leaves the first material 48 as a supersonic flame. The flame front accelerates to become a supersonic flame propagating towards the second material 52. The pressure increases with the transition from conflagration (deflagration) to detonation (explosion). The detonation (explosion) causing the supersonic wave creates a powerful pressure wave that travels ahead of the propagating flame increasing the temperature of the first material above an auto ignition temperature of the first material 48.

FIG. 10C illustrates the second material 52 detonating (exploding) due to the detonation (explosion) of the first material 48. In certain embodiments, the detonating (explosion) wave produced by the second material 52 travels at greater than the speed of sound. The detonating (explosion) wave produced by the second material 52 produces a similar detonating (explosion) wave in the wall segment 44. The detonating (explosion) wave continues through the wall segment 44 and imparts its velocity to the plurality of particles 60 disposed against the outer surface 56 on the body 14. The detonating (explosion) wave then ejects (emits) the plurality of particles 60 from the body 14 at an initial speed that exceeds the speed of sound.

A method for manufacturing the accelerator module 12 is described below. Of course, other methods that include more or less steps and/or a different order of the steps also fall within the scope of the disclosure.

In certain embodiments, the method for manufacturing the accelerator module 12 begins by providing the base 16. The base 16 includes the chamber 45 formed in part by the bottom surface 54. The bottom surface 54 is spaced from the outer surface 56 by the wall segment 45. A distal end of the ejection tube 58 is configured for placement against the tissue. In certain embodiments, the ejection tube 58 is configured to support the plurality of particles 60.

The second material 52 is loaded into the second portion 50 of the chamber 45. In certain embodiments, the second material 52 is in contact with the bottom surface 54. In certain embodiments, the second material 52 is the detonating output material. In certain embodiments, the second material 52 is a dry powder. In certain embodiments, the second material 52 is pentaerythritol tetranitrate (PETN). In certain embodiments, the second material 52 is pressed against the bottom surface 54 of the chamber 45 at a required pressure to achieve a desired degree of compaction.

The first material 48 is loaded into the first portion 46 of the chamber 45 on top of the second material 52. In certain embodiments, the first material 48 is in contact with the second material 52. In certain embodiments, the first material 48 is the deflagration-to-detonation material. In certain embodiments, the first material 48 is a dry powder. In certain embodiments, the first material 48 is lead azide. In certain embodiments, the first material 48 is copper (I) 5-nitrotetrazolate (DBX-1). In certain embodiments, the first material 48 is pressed against the second material 52 in the chamber 45 at a required pressure to achieve a desired degree of compaction. Of course, the first material 48 and the second material 52 can be pressed at the same time into the chamber 45 to achieve the desired degree of compaction without separately pressing the second material 52.

Next, the initiator 30 is installed in the opening 26 of the base 16. In certain embodiments, at least a portion of the casing 32 is located within the chamber 45 of the receptacle 20. In certain embodiments, the casing 32 is disposed in close proximity to the first material 48.

In certain embodiments, the initiator 30 is installed together with the seal 24 in the opening 26 in the base 16. In certain embodiments, the seal 24 is a gasket or O-ring. In certain embodiments, the initiator 30 is held in place by installing the cap 18. In certain embodiments, the cap 18 includes threads that are complementary to threads on the base 16.

The plurality of particle 60 are installed in the ejection tube 58. If the gene gun 10 is to be used with the ejection tube 58 pointing in an upward direction, the plurality of particle 60 can be poured onto the exposed body 14 and held against the outer surface 56 of the body 14 by gravity. In certain embodiments, the plurality of particles 60 are poured onto the outer surface 56 of the body 14 in the ejection tube 58.

To use the gene gun 10 in any orientation in certain embodiments, the plurality of particles 60 are held in place against the outer surface 56 of the body 14. In this way, the detonating (explosion) wave exiting the wall segment 45 will transfer to the plurality of particles 60.

Figure 11:
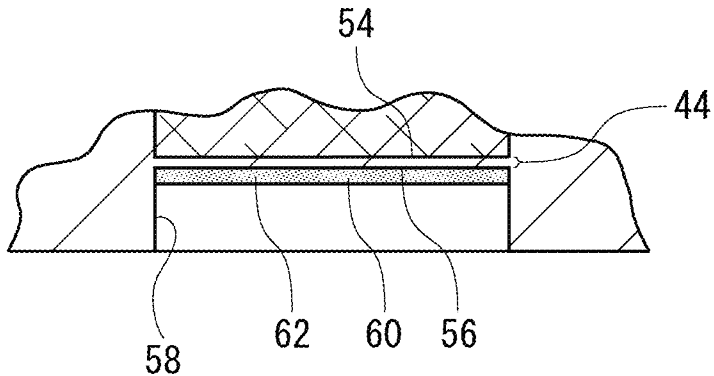
FIG. 11 illustrates another embodiment of the ejection tube that includes an adhesive for inhibiting the plurality of particles from falling out of the ejection tube prior to ignition of the accelerator module.

FIG. 11 illustrates another embodiment of the ejection tube 58 that includes an adhesive 62 for inhibiting the plurality of particles 60 from falling out of the ejection tube 58 prior to ignition of the accelerator module 12. The adhesive 62 holds the plurality of particles 60 in place against the outer surface 56. In certain embodiments, when the gene gun 10 is operated, the adhesive 62 can break away and/or be vaporized leaving the plurality of particles 60 to continue traveling at the velocity of the detonating (explosion) wave. In certain embodiments, the adhesive 62 is less dense than the plurality of particles 60 and quickly disperses or slows down. In this way, the adhesive 62 does not impede the movement of the plurality of particles 60.

Figure 12:
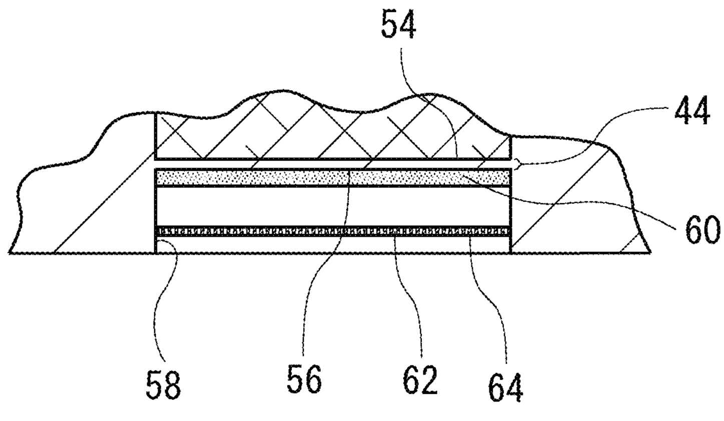
FIG. 12 is similar to FIG. 11 except a screen is disposed over the distal end of the ejection tube.

FIG. 12 is similar to FIG. 11 except a screen 64 is disposed over the distal end of the ejection tube 58 and affixed thereto. In the illustrated embodiment, the adhesive 62 is retained on the screen 64. In certain embodiments, the screen 64 has a plurality of pores. In certain embodiments, the plurality of pores are micro pores. In certain embodiments, the screen 64 has a fine mesh to allow the plurality of particles 60 to passthrough the pores in the screen 64 unimpeded.

Figure 13:
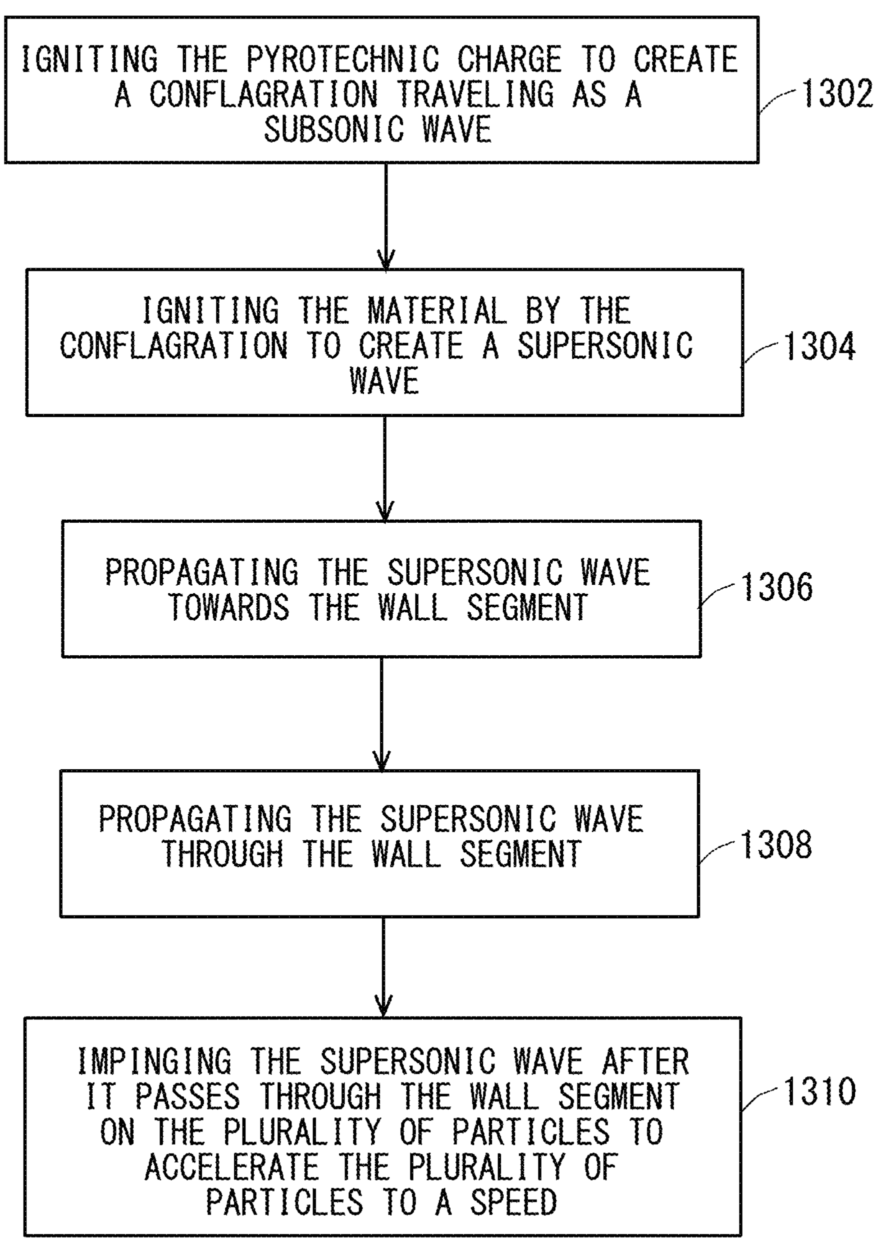
FIG. 13 is a drawing that represents the propagation of energy through the accelerator module.

FIG. 13 is a drawing that represents a method for the propagation of energy through the accelerator module 12. The method delivers the plurality of particles 60 to cells within tissue using a portable device such as the gene gun 10. The method begins at step 1302 by igniting the pyrotechnic charge 34 disposed in the portable device to create a conflagration traveling as a subsonic wave. In certain embodiments, the at least one pin 38 receives the electrical input in the form of an electrical firing pulse. The pyrotechnic charge 34 creates the conflagration when ignited. Once the pyrotechnic charge 34 is triggered, the pressure released by the pyrotechnic charge 34 in the casing 32 breaks the casing 32 allowing the deflagration to propagate at subsonic speed along the axis 28 towards the first material 48 in the chamber 45. The deflagration caused by the pyrotechnic charge 34 creates a propagating subsonic flame. In this way, the subsonic flame propagates along the axis 28 towards the material 48, 52 disposed in the chamber 45.

Next, the material 48, 52 is ignited by the conflagration to create a supersonic wave at step 1304. In certain embodiments, the first material 48 is the deflagration-to-detonation transition (DDT) material. Once ignited, the first material 48 transitions from deflagration to detonation (explosion). While the first material 48 is ignited by the subsonic flame, the subsonic flame eventually transitions to detonation (explosion). The flame front accelerates to become a supersonic flame propagating through the second material 52.

Next at step 1306, the supersonic wave continues to propagate along the axis 28 towards the wall segment 45 of the portable device. At step 1308, the method continues by propagating the supersonic wave through the wall segment 45 without rupturing the wall segment 45. The method continues at step 1310 by impinging the supersonic wave after it passes through the wall segment 45 on the plurality of particles 60 to accelerate the plurality of particles 60 to a speed. In this way, the detonating (explosion) wave ejects the plurality of particles 60 from the body 14 at an initial speed that exceeds the speed of sound.

In certain embodiments, the method further includes penetrating the tissue with the plurality of particles 60. In certain embodiments, the method further includes penetrating the cells of the tissue with the plurality of particles 60. In certain embodiments, the speed is a supersonic speed. In certain embodiments, the supersonic speed exceeds a speed of sound in hydrogen. In certain embodiments, the material 48, 52 is one or more of the deflagration-to-detonation transition (DDT) material and the detonating output material. In certain embodiments, the plurality of particles 60 are in contact with the outer surface 56 of the portable device and generally aligned (arranged in line) with the axis 28.

Regarding the above-described embodiments, the following supplementary notes will be further described.

(Supplementary Note 1)

An accelerator module configured to be coupled to an initiator module and create a supersonic wave from a subsonic wave created by the initiator module, the supersonic wave being configured to deliver particles to cells within tissue, the accelerator module including:

a body having a propagation axis and defining a receptacle with a bottom surface, the receptacle including a first portion and a second portion disposed between the first portion and the bottom surface;

a first material disposed in the first portion;

a second material disposed in the second portion;

a wall segment at least partially defined between the bottom surface of the receptacle and an outer surface of the body; and a plurality of doped metal particles in contact with the outer surface of the body and generally aligned with the bottom surface along the propagation axis, the first material and the second material being configured to be triggered by the subsonic wave created by the initiator module to create the supersonic wave, the supersonic wave being configured to pass through the wall segment to then accelerate the plurality of doped metal particles to a speed.

(Supplementary Note 2)

The accelerator module as set forth in Supplementary note 1, wherein the speed is a supersonic speed.

(Supplementary Note 3)

The accelerator module as set forth in Supplementary note 1 or 2, wherein the speed is sufficient to penetrate the cells within the tissue.

(Supplementary Note 4)

The accelerator module as set forth in any one of Supplementary notes 1 to 3, wherein the first material is a deflagration-to-detonation transition (DDT) material.

(Supplementary Note 5)

The accelerator module as set forth in Supplementary note 4, wherein the deflagration-to-detonation transition material includes a dry powder.

(Supplementary Note 6)

The accelerator module as set forth in Supplementary note 4 or 5, wherein the deflagration-to-detonation transition material includes lead azide.

(Supplementary Note 7)

The accelerator module as set forth in any one of Supplementary notes 4 to 6, wherein the deflagration-to-detonation transition material includes copper (I) 5-nitrotetrazolate (DBX-1).

(Supplementary Note 8)

The accelerator module as set forth in any one of Supplementary notes 1 to 7, wherein the second material is a detonating output material.

(Supplementary Note 9)

The accelerator module as set forth in Supplementary note 8, wherein the detonating output material is a dry powder.

(Supplementary Note 10)

The accelerator module as set forth in Supplementary note 8 or 9, wherein the detonating material includes pentaerythritol tetranitrate (PETN).

(Supplementary Note 11)

The accelerator module as set forth in any one of Supplementary notes 1 to 10, wherein the wall segment includes stainless steel.

(Supplementary Note 12)

The accelerator module as set forth in any one of Supplementary notes 1 to 11, wherein the body includes the wall segment.

(Supplementary Note 13)

The accelerator module as set forth in any one of Supplementary notes 1 to 12, wherein a material of the wall segment is selected so that the wall segment does not rupture when the supersonic wave passes therethrough.

(Supplementary Note 14)

The accelerator module as set forth in any one of Supplementary notes 1 to 13, wherein a thickness of the wall segment is selected so that the wall segment does not rupture when the supersonic wave passes therethrough.

(Supplementary Note 15)

The accelerator module as set forth in any one of Supplementary notes 1 to 14, wherein the body includes a base and a cap, and the cap is configured to be secured to the base forming at least a portion of the receptacle between the base and the cap.

(Supplementary Note 16)

The accelerator module as set forth in Supplementary note 15, wherein the receptacle is further configured to receive at least a portion of the initiator module when the cap is not secured to the base, and the receptacle is configured to secure the initiator module relative to the body when the cap is secured to the base.

(Supplementary Note 17)

The accelerator module as set forth in any one of Supplementary notes 1 to 16, wherein the body includes an opening into the receptacle, and the opening is sized and shaped for a portion of the initiator module to pass through the opening when the initiator module is coupled to the accelerator module.

(Supplementary Note 18)

The accelerator module as set forth in Supplementary note 17, wherein the portion of the initiator module is at least one electrical pin.

(Supplementary Note 19)

The accelerator module as set forth in any one of Supplementary notes 1 to 18, wherein the body includes an ejection tube disposed on an opposite side of the wall segment from the receptacle, the ejection tube is aligned with the propagation axis, and the plurality of doped metal particles are disposed in the ejection tube.

(Supplementary Note 20)

The accelerator module as set forth in Supplementary note 19, wherein the ejection tube is a straight cylinder, and wherein a cross-section of the ejection tube has a similar size to a cross-section of the receptacle.

(Supplementary Note 21)

The accelerator module as set forth in any one of Supplementary notes 1 to 20, wherein the accelerator module is a component of a gene gun.

(Supplementary Note 22)

The accelerator module as set forth in any one of Supplementary notes 1 to 21, wherein the first portion and the second portion are aligned along the propagation axis.

(Supplementary Note 23)

The accelerator module as set forth in any one of Supplementary notes 1 to 22, wherein the bottom surface is perpendicular to the propagation axis.

(Supplementary Note 24)

The accelerator module as set forth in any one of Supplementary notes 1 to 23 further including an adhesive disposed on at least a portion of the outer surface of the body, wherein the plurality of doped metal particles is suspended in the adhesive.

(Supplementary Note 25)

The accelerator module as set forth in any one of Supplementary notes 1 to 24 further including:

- a screen secured to the body in a position covering the plurality of doped metal particles; and
- an adhesive disposed on the screen to prevent the plurality of doped metal particles from passing through the screen in the absence of the supersonic wave.

(Supplementary Note 26)

The accelerator module as set forth in any one of Supplementary notes 1 to 25 further including a seal, wherein the receptacle is further configured to receive at least a portion of the initiator module, and the seal is disposed in the receptacle to form a seal with the initiator module.

(Supplementary Note 27)

The accelerator module as set forth in any one of Supplementary notes 1 to 26, wherein a particle of the plurality of doped metal particles has a diameter of about 1 micron.

(Supplementary Note 28)

The accelerator module as set forth in any one of Supplementary notes 1 to 27, wherein the plurality of doped metal particles includes gold.

(Supplementary Note 29)

The accelerator module as set forth in any one of Supplementary notes 1 to 28, wherein the plurality of doped metal particles includes tungsten.

(Supplementary Note 30)

The accelerator module as set forth in any one of Supplementary notes 1 to 29, wherein the plurality of doped metal particles includes a chemical.

(Supplementary Note 31)

The accelerator module as set forth in Supplementary note 30, wherein the chemical is DNA.

(Supplementary Note 32)

The accelerator module as set forth in any one of Supplementary notes 1 to 31, wherein the initiator module is an electro explosive device (EED).

(Supplementary Note 33)

The accelerator module as set forth in Supplementary note 32, wherein the electro explosive device (EED) includes an electrical input and a pyrotechnic output.

(Supplementary Note 34)

The accelerator module as set forth in Supplementary note 33, wherein the pyrotechnic output is a mixture of zirconium and potassium perchlorate.

(Supplementary Note 35)

The accelerator module as set forth in Supplementary note 33 or 34, wherein the electro explosive device (EED) includes a casing, and the pyrotechnic output is disposed in the casing.

(Supplementary Note 36)

The accelerator module as set forth in Supplementary note 35, wherein the casing is metal.

(Supplementary Note 37)

An accelerator module including:

- a body having a propagation axis and defining a receptacle with a bottom surface, the propagation axis passing through the bottom surface;
- a material disposed in the receptacle and configured to at least in part create a detonating wave travelling at supersonic speed;
- a wall segment at least partially defined between the bottom surface of the receptacle and an outer surface of the body, the wall segment being sized to allow the detonating wave to travel therethrough without fracturing the wall segment; and
- a plurality of doped metal particles disposed on the opposite side of the wall segment from the receptacle and generally aligned with the propagation axis.

(Supplementary Note 38)

The accelerator module as set forth in Supplementary note 37, wherein the plurality of doped metal particles is in contact with the outer surface of the body.

(Supplementary Note 39)

The accelerator module as set forth in Supplementary note 37 or 38, wherein the propagation axis is perpendicular to the bottom surface.

(Supplementary Note 40)

The accelerator module as set forth in any one of Supplementary notes 37 to 39, wherein the material includes a deflagration-to-detonation transition material (DDT).

(Supplementary Note 41)

The accelerator module as set forth in any one of Supplementary notes 37 to 40, wherein the material includes a detonating output material.

(Supplementary Note 42)

The accelerator module as set forth in any one of Supplementary notes 37 to 41, wherein the receptacle includes a first portion and a second portion, the second portion is disposed between the first portion and the bottom surface, the material includes a first material and a second material, the first material is disposed in the first portion, and the second material is disposed in the second portion.

(Supplementary Note 43)

The accelerator module as set forth in any one of Supplementary notes 37 to 42, wherein the accelerator module is configured to be coupled to an initiator module, and the initiator module is configured so that the material is triggered by a subsonic wave.

(Supplementary Note 44)

The accelerator module as set forth in any one of Supplementary notes 37 to 43, wherein the detonating wave accelerates the plurality of doped metal particles after passing through the wall segment.

(Supplementary Note 45)

A method for delivering a plurality of doped metal particles to cells (preferably, cells within tissue. An aspect excluding cells (preferably, cells within tissue) in a state of being present in an individual (living body) of humans is preferable. An aspect excluding cells (preferably, cells within tissues) in a state of being present in an individual (living body) of animals is preferable) using a portable device, the method including:

igniting a pyrotechnic charge disposed in the portable device to create a subsonic wave, the subsonic wave propagating along an axis towards a material disposed in the portable device;

igniting the material with the subsonic wave to create a supersonic wave, the supersonic wave continuing to propagate along the axis towards a wall segment of the portable device; and propagating the supersonic wave through the wall segment without rupturing the wall segment, and impinging the supersonic wave after passing through the wall segment on the plurality of doped metal particles to accelerate the plurality of doped metal particles to a speed.

(Supplementary Note 46)

The method as set forth in Supplementary note 45 further including configuring the plurality of doped metal particles to penetrate through tissue.

(Supplementary Note 47)

The method as set forth in Supplementary note 46 further including configuring the plurality of doped metal particles to penetrate through cells of the tissue.

(Supplementary Note 48)

The method as set forth in any one of Supplementary notes 45 to 47, wherein the speed is a supersonic speed.

(Supplementary Note 49)

The method as set forth in Supplementary note 48, wherein the supersonic speed exceeds a speed of sound in hydrogen (Supplementary Note 50)

The method as set forth in any one of Supplementary notes 45 to 49, wherein the material is a deflagration-to-detonation transition material (DDT).

(Supplementary Note 51)

The method as set forth in any one of Supplementary notes 45 to 50, wherein the material is a detonating output material.

(Supplementary Note 52)

The method as set forth in any one of Supplementary notes 45 to 51, wherein the plurality of doped particles is in contact with an outer surface of the portable device and generally aligned with the axis.

(Supplementary Note 53)

A gene gun having a propagation axis extending at least between a pyrotechnic charge and a plurality of doped metal particles, the gene gun including:

a deflagration-to-detonation transition material (DDT) disposed generally along the propagation axis;

a detonating output material disposed on an opposite side of the deflagration-to-detonation transition material (DDT) from the pyrotechnic charge and disposed generally along the propagation axis; and a wall segment separating the detonating output material from the plurality of doped metal particles.

(Supplementary Note 54)

The gene gun as set forth in Supplementary note 53, wherein the wall segment is sized not to rupture in response to detonation of the detonating output material.

(Supplementary Note 55)

An accelerator module configured to be coupled to an initiator module and deliver particles, a plurality of doped metal particles to cells within tissue, the accelerator module including:

a body having a propagation axis and defining a receptacle with a bottom surface;

a material disposed in the receptacle and creating a supersonic wave by being ignited by the subsonic wave created by the initiator module; and a wall segment extending through the propagation axis and separating an inside and an outside of the receptacle, an outer surface of the wall segment on which a plurality of doped metal particles being able to be disposed to be aligned along the propagation axis, the supersonic wave created by the material creating the supersonic wave propagating through the wall segment, and after passing therethrough, impinging on the plurality of doped metal particles, to thereby accelerate the plurality of doped metal particles.

(Supplementary Note 56)

The accelerator module as set forth in Supplementary note 55, wherein the material creating the supersonic wave creates a deflagrating wave traveling at a supersonic speed by being ignited by the subsonic wave.

(Supplementary Note 57)

The accelerator module as set forth in Supplementary note 55 or 56, wherein the material creating the supersonic wave is a dry powder.

(Supplementary Note 58)

The accelerator module as set forth in any one of Supplementary notes 55 to 57, wherein the bottom surface is perpendicular to the propagation axis.

(Supplementary Note 59)

The accelerator module as set forth in any one of Supplementary notes 55 to 58, wherein the wall segment is configured not to rupture when the supersonic wave passes therethrough.

(Supplementary Note 60)

The accelerator module as set forth in any one of Supplementary notes 55 to 59, wherein the body includes an ejection tube disposed on an opposite side of the wall segment from the receptacle, the ejection tube is aligned with the propagation axis, and the plurality of doped metal particles are disposed in the ejection tube.

(Supplementary Note 61)

The accelerator module as set forth in any one of Supplementary notes 55 to 60, wherein the receptacle includes a first portion and a second portion disposed between the first portion and the bottom surface, and the material includes a first material disposed in the first portion and a second material disposed in the second portion.

(Supplementary Note 62)

The accelerator module as set forth in Supplementary note 61, wherein the first portion and the second portion are aligned along the propagation axis.

(Supplementary Note 63)

The accelerator module as set forth in Supplementary note 61 or 62, wherein the first material is a deflagration-to-detonation transition (DDT) material.

(Supplementary Note 64)

The accelerator module as set forth in Supplementary note 63, wherein the deflagration-to-detonation transition (DDT) material includes at least either lead azide or copper (I) 5-nitrotetrazolate (DBX-1).

(Supplementary Note 65)

The accelerator module as set forth in any one of Supplementary notes 61 to 64, wherein the second material is a detonating output material.

(Supplementary Note 66)

The accelerator module as set forth in Supplementary note 65, wherein the detonating output material includes pentaerythritol tetranitrate (PETN).

(Supplementary Note 67)

The accelerator module as set forth in any one of Supplementary notes 55 to 66, wherein the initiator module includes a pyrotechnic charge and ignites the pyrotechnic charge to create the subsonic wave.

(Supplementary Note 68)

A gene gun including the accelerator module as set forth in any one of Supplementary notes 55 to 67.

(Supplementary Note 69)

A method for delivering a plurality of doped metal particles to cells (preferably, cells within tissue. An aspect excluding cells (preferably, cells within tissue) in a state of being present in an individual (living body) of humans is preferable. An aspect excluding cells (preferably, cells within tissues) in a state of being present in an individual (living body) of animals is preferable) using a portable device, the method including:

- igniting a pyrotechnic charge disposed in the portable device to create a subsonic wave, the subsonic wave propagating along an axis towards a material disposed in the portable device;
- igniting the material with the subsonic wave to create a supersonic wave, the supersonic wave continuing to propagate along the axis towards a wall segment of the portable device; and
- propagating the supersonic wave through the wall segment, and impinging the supersonic wave after passing through the wall segment on the plurality of doped metal particles to accelerate the plurality of doped metal particles.

Terminology

Although certain embodiments and examples are disclosed herein, inventive subject matter extends beyond the examples in the specifically disclosed embodiments to other alternative embodiments and/or uses, and to modifications and equivalents thereof. Thus, the scope of the claims appended hereto is not limited by any of the particular embodiments described above. For example, in any method or process disclosed herein, the acts or operations (acts) of the method or process may be performed in any suitable sequence and are not necessarily limited to any particular disclosed sequence. Various operations (acts) may be described as multiple discrete operations (acts) in turn, in a manner that may be helpful in understanding certain embodiments; however, the order of description should not be construed to imply that these operations (acts) are order dependent. Additionally, the structures, systems, and/or devices described herein may be embodied as integrated components or as separate components. For purposes of comparing various embodiments, certain aspects and advantages of these embodiments are described. Thus, for example, various embodiments may be carried out in a manner that achieves or optimizes one aspect, advantage, or group of advantages as taught herein without necessarily achieving other aspects or advantages as may also be taught or suggested herein.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. Not necessarily all such aspects or advantages are achieved by any particular embodiment. For example, one or more of the features including 1) a combination of DDT and PETN; 2) a pyrotechnic charge and DDT located downstream of the pyrotechnic charge with PETN located downstream of the DDT; 3) an accelerator module configured to receive an initiator module; 4) a wall segment separating the detonating output material from the doped metal particles; 5) a detonating (explosion) wave passing through a wall segment without rupturing the wall element; 6) doped metal particles achieving speeds exceeding sonic speeds; 7) doped metal particles located downstream of the detonating (explosion) wave; and/or 8) igniting a detonating (explosion) wave using a deflagration. Therefore, the protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a subcombination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of this disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

For expository purposes, the term "horizontal" as used herein is defined as a plane parallel to the plane or surface of the floor or ground of the area in which the device being described is used or the method being described is performed, regardless of its orientation. The term "floor" can be interchanged with the term "ground." The term "vertical" refers to a direction perpendicular to the horizontal as just defined. Terms such as "above," "below," "bottom," "top," "side," "higher," "lower," "upper," "over," and "under," are defined with respect to the horizontal plane.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without other input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" issued in its inclusive sense (and not in its exclusive sense) so that when used, for example, to connect a list of elements, the term "or" means one, some, or all of the elements in the list.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately," "about," "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, 0.1 degree, or otherwise.

Although the gene gun has been disclosed in the context of certain embodiments and examples, it will be understood by those skilled in the art that the gene gun extends beyond the specifically disclosed embodiments to other alternative embodiments and/or uses of the embodiments and certain modifications and equivalents thereof. Accordingly, it is intended that the scope of the gene gun herein-disclosed should not be limited by the particular disclosed embodiments described above, but should be determined only by a fair reading of the claims that follow.

Each embodiment disclosed in the present description can be combined with each of the features disclosed in the present description.

REFERENCE SIGNS LIST

10 Gene gun
11 Handle
12 Accelerator module
14 Body
16 Base
20 Receptacle
30 Initiator
32 Casing
34 Pyrotechnic charge
44 Wall segment
45 Chamber
46 First portion
48 First material
50 Second portion
52 Second material
54 Bottom surface
58 Ejection tube
60 Particle

The invention claimed is:

1. A gene gun comprising:
- a body having a propagation axis and defining a receptacle with a bottom surface;
- an initiator module comprising a pyrotechnic charge and a casing that houses the pyrotechnic charge;
- a first material disposed in a first portion of the receptacle;
- a wall segment extending through the propagation axis and separating an inside and an outside of the receptacle;
- an outer surface of the wall segment on which a plurality of doped metal particles are disposed to be aligned along the propagation axis; and
- a gap between the casing and the first material,
- wherein the initiator module is configured to ignite the pyrotechnic charge to cause the casing that houses the pyrotechnic charge to rupture and create a subsonic wave, which is discharged from the casing, wherein the gap between the casing and the first material is configured to allow the casing to rupture, wherein the subsonic wave propagates across the gap to the first material,
- wherein the first material is configured to be ignited by the subsonic wave so as to create a supersonic wave, which propagates through the wall segment and impinges on the plurality of doped metal particles to accelerate the plurality of doped metal particles,
- wherein the gene gun is configured to deliver the plurality of doped metal particles accelerated by the supersonic wave to cells within a tissue.

2. The gene gun according to claim 1, wherein the first material creating the supersonic wave is a dry powder.

3. The gene gun according to claim 1, wherein the bottom surface is perpendicular to the propagation axis.

4. The gene gun according to claim 1, wherein the wall segment is configured not to rupture when the supersonic wave passes therethrough.

5. The gene gun according to claim 1, wherein the body includes an ejection tube disposed on an opposite side of the wall segment from the receptacle, the ejection tube is aligned with the propagation axis, and the plurality of doped metal particles are disposed in the ejection tube.

6. The gene gun according to claim 1, wherein:

the receptacle further includes a second portion disposed between the first portion and the bottom surface, and a second material disposed in the second portion, wherein the second material is configured to create a supersonic wave from the subsonic wave.

7. The gene gun according to claim 6, wherein the first portion and the second portion are aligned along the propagation axis.

8. The gene gun according to claim 6, wherein the first material is a deflagration-to-detonation transition (DDT) material.

9. The gene gun according to claim 8, wherein the deflagration-to-detonation transition (DDT) material includes at least either lead azide or copper (I) 5-nitrotetrazolate (DBX-1).

10. The gene gun according to claim 6, wherein the second material is a detonating output material.

11. The gene gun according to claim 10, wherein the detonating output material includes pentaerythritol tetranitrate (PETN).

12. The gene gun according to claim 6, wherein the second material creating the supersonic wave is a dry powder.

13. The gene gun according to claim 6, wherein the bottom surface is perpendicular to the propagation axis.

14. The gene gun according to claim 6, wherein the wall segment is configured not to rupture when the supersonic wave passes therethrough.

15. A method of delivering a plurality of doped metal particles to cells within a tissue, the method comprising:

providing a gene gun according to claim 1, igniting the pyrotechnic charge to cause the casing that houses the pyrotechnic charge to rupture and create the subsonic wave, discharging the subsonic wave from the casing, wherein the subsonic wave propagates across the gap to the first material, the subsonic wave igniting the first material to create a supersonic wave, propagating the supersonic wave through the wall segment to impinge on the plurality of doped metal particles, thereby accelerating the plurality of doped metal particles, delivering the accelerated plurality of doped metal particles to the cells within the tissue.

* * * * *